US009029627B2

(12) United States Patent
Okabe et al.

(10) Patent No.: US 9,029,627 B2
(45) Date of Patent: May 12, 2015

(54) MODEL ANIMAL FOR PREGNANCY-INDUCED HYPERTENSION SYNDROME, AND TREATMENT METHOD THEREFOR

(75) Inventors: Masaru Okabe, Minoo (JP); Masahito Ikawa, Settsu (JP); Tadashi Kimura, Osaka (JP); Keiichi Kumasawa, Toyonaka (JP)

(73) Assignees: Masaru Okabe, Osaka (JP); Masahito Ikawa, Osaka (JP); Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 13/581,510

(22) PCT Filed: Mar. 4, 2011

(86) PCT No.: PCT/JP2011/055087
§ 371 (c)(1),
(2), (4) Date: Nov. 13, 2012

(87) PCT Pub. No.: WO2011/108711
PCT Pub. Date: Sep. 9, 2011

(65) Prior Publication Data
US 2013/0198874 A1    Aug. 1, 2013

(30) Foreign Application Priority Data

Mar. 4, 2010    (JP) ................. 2010-048237

(51) Int. Cl.
| | | |
|---|---|---|
| *A01K 67/027* | (2006.01) | |
| *C12N 15/85* | (2006.01) | |
| *A61D 19/04* | (2006.01) | |
| *C12N 9/12* | (2006.01) | |

(52) U.S. Cl.
CPC ....... *A01K 67/0278* (2013.01); *A01K 2227/105* (2013.01); *A01K 2267/0375* (2013.01); *A01K 2267/0393* (2013.01); *C12N 15/8509* (2013.01); *C12N 2799/027* (2013.01); *A61D 19/04* (2013.01); *A01K 67/0271* (2013.01); *A01K 67/0275* (2013.01); *C12N 9/1205* (2013.01); *A01K 2207/12* (2013.01); *A01K 2217/052* (2013.01)

(58) Field of Classification Search
CPC ................ A61K 38/00; C12N 15/86; C12N 2710/16643; G01N 2800/368; G01N 33/5091
See application file for complete search history.

(56) References Cited

U.S. PATENT DOCUMENTS

2009/0013418 A1* 1/2009 Okabe et al. ............. 800/3

FOREIGN PATENT DOCUMENTS

| JP | 2006-511615 | 4/2006 | |
| JP | 2007-518769 | 7/2007 | |
| JP | 2007-518769 A * | 7/2007 | ............. A61K 38/16 |
| WO | 2004/008946 | 1/2004 | |
| WO | 2005/070450 | 8/2005 | |
| WO | 2007/020786 | 2/2007 | |

OTHER PUBLICATIONS

Kobayashi et al., "Byotaibetsu ni Mita DIC no Shindan to Chiruo 6 Sanfujinka Ryoiki" Biomedicine & Therapeutics (2007) 41(3):265-268.
Suzuki et al., "sFlt-1 Kajo Hatsugen ni yoru Ninshin Koketsuatsu Jinsho-yo Mouse Model ni Okeru, Kekkan Shinsei Inshi Toyo ni yoru Kecchu NO eno Eikyo" Acta Obstetrica et Gynaecologia Japonica (Feb. 2010) 62(2), p. 492, pp. 2 to 84.
Kodama et al., "Atorvastatin Increases Plasma sFlt-1 and Decreases VEGF and PIGF in Association with Improvement of Ventricular Function in Acute Myocardial Infarction" Circ J, (2007) 71(Supp 1):670.
Kodama et al., "Atorvastation increases soluble Fms-like tyrosine kinase-1 and decreases vascular endothelial growth factor and placental growth factor in association with improvement of ventricular function in acute myocardial infarction" Journal of the American College of Cardiology, (2006), 48(1):43-50.
Loboda et al., "Angiogenic transcriptome of human microvascular endothelial cells: Effect of hypoxia, modulation by atorvastatin" Vascular Pharmacology (2006) 44(4):206-214.
Maynard Se, et al., "Excess placental soluble fms-like typrosine kinase 1 (sFlt1) may contribute to endothelial dysfunction, hypertension, and proeinuria in preclampsia" J. Clin Invest (Mar. 2003) 111(5):649-58.
Falcao et al., "Mice Overexpressing Both Human Angiotensinogen and Human Renin as a Model of Superimposed Preeclampsia on Chronic Hypertension" Hypertension (2009) 54:1401-1407.
Redecha et al., "Pravastatin prevents miscarriages in mice: role of tissue factor in placental and fetal injury" Blood (2009) 113:4101-4109.

(Continued)

*Primary Examiner* — Marcia S Noble
*Assistant Examiner* — Chi-Feng Hsu
(74) *Attorney, Agent, or Firm* — Karl Bozicevic; Bozicevic Field & Francis LLP

(57) ABSTRACT

A lentiviral vector was used to produce non-human animals that express human sFLT1 specifically in the murine placenta, to provide model animals of diseases such as pregnancy-induced hypertension syndrome that are close to the clinical conditions, methods for producing the model animals, methods of screening for candidate compounds as therapeutic agents for diseases such as pregnancy-induced hypertension syndrome by using the model animals, and therapeutic agents for diseases such as pregnancy-induced hypertension syndrome. As a result, the model animals were found to exhibit symptoms that are very close to the clinical conditions in human, which are presentation of hypertension as well as placental insufficiency, intrauterine growth retardation, glomerulosclerosis, and proteinuria during pregnancy, and improvement of those symptoms postpartum. Furthermore, when pravastatin was administered to this model animal, it was found that diseases such as pregnancy-induced hypertension syndrome were improved by the activation of placenta-derived growth factor (PIGF) which antagonizes sFLT1.

5 Claims, 5 Drawing Sheets

(56) References Cited

OTHER PUBLICATIONS

International Search Report for PCT/JP2011/055087 completed May 6, 2011 (mailed May 17, 2011).
Khan et al., "WHO analysis of causes of maternal death_a systematic review" The Lancet (Apr. 1, 2006) 367 (9516):1066-74.
Kumasawa et al., "Pravastatin induces placental growth factor (PGF) and ameliorates preeclampsia in a mouse model" Proc Natl Acad SCI USA (Jan. 25, 2011) 108(4):1451-5 (Epub Dec. 27, 2010).
Levine et al., "Circulating Angiogenic Factors and the Risk of Preeclampsia" N Engl J Med (Feb. 12, 2004) 350(7):672-83.
Morioka et al., "Placenta-Specific Gene Activation and Inactiviation Using Integrase-Defective Lentiviral Vectoras with the Cre/LoxP System" Genesis (Dec. 2009) 47(12):793-8.
Okada et al., "Complementation of placental defects and embryonic lethality by trophoblast-specific lentiviral gene transfer" Nat Biotechnol (Feb. 2007) 25(2):233-7 (Epub Jan. 14, 2007).
U.S. Appl. 14/332,738, filed Jul. 16, 2014 entitled "Trophectodermal Cell-Specific Gene Transfer Methods" (Inventors Okabe, Masaru and Ikawa, Masahito).

* cited by examiner

```
                         SEQUENCE LISTING

<160> NUMBER OF SEQ ID NOS: 22

<210> SEQ ID NO 1
<211> LENGTH: 2064
<212> TYPE: DNA
<213> ORGANISM: Homo sapiens

<400> SEQUENCE: 1
atggtcagct actgggacac cggggtcctg ctgtgcgcgc tgctcagctg tctgcttctc      60
acaggatcta gttcaggttc aaaattaaaa gatcctgaac tgagtttaaa aggcacccag     120
cacatcatgc aagcaggcca gacactgcat ctccaatgca gggggaagc  agcccataaa     180 tggtctttgc ctgaaatggt gagtaaggaa agcgaaaggc tgagcataac taaatctgcc     240
tgtggaagaa atggcaaaca attctgcagt actttaacct tgaacacagc tcaagcaaac     300
cacactggct tctacagctg caaatatcta gctgtaccta cttcaaagaa gaaggaaaca     360
gaatctgcaa tctatatatt tattagtgat acaggtagac ctttcgtaga gatgtacagt     420
gaaatccccg aaattataca catgactgaa ggaagggagc tcgtcattcc ctgccgggtt     480
acgtcaccta acatcactgt tactttaaaa aagtttccac ttgacacttt gatccctgat     540
ggaaaacgca taatctggga cagtagaaag ggcttcatca tatcaaatgc aacgtacaaa     600
gaaatagggc ttctgacctg tgaagcaaca gtcaatgggc atttgtataa gacaaactat     660
ctcacacatc gacaaaccaa tacaatcata gatgtccaaa taagcacacc acgcccagtc     720
aaattactta gaggccatac tcttgtcctc aattgtactg ctaccactcc cttgaacacg     780
agagttcaaa tgacctggag ttaccctgat gaaaaaaata gagagcttc  cgtaaggcga     840 cgaattgacc aaagcaattc ccatgccaac atattctaca gtgttcttac tattgacaaa     900
atgcagaaca aagacaaagg actttatact tgtcgtgtaa ggagtggacc atcattcaaa     960
tctgttaaca cctcagtgca tatatatgat aaagcattca tcactgtgaa acatcgaaaa    1020
cagcaggtgc ttgaaaccgt agctggcaag cggtcttacc ggctctctat gaaagtgaag    1080 gcatttcct  cgccggaagt tgtatggtta aaagatgggt tacctgcgac tgagaaatct    1140
gctcgctatt tgactcgtgg ctactcgtta attatcaagg acgtaactga agaggatgca    1200
gggaattata caatcttgct gagcataaaa cagtcaaatg tgtttaaaaa cctcactgcc    1260
actctaattg tcaatgtgaa accccagatt tacgaaaagg ccgtgtcatc gtttccagac    1320
```

```
ccggctctct acccactggg cagcagacaa atcctgactt gtaccgcata tggtatccct    1380
caacctacaa tcaagtggtt ctggcacccc tgtaaccata atcattccga agcaaggtgt    1440
gacttttgtt ccaataatga agagtccttt atcctggatg ctgacagcaa catgggaaac    1500
agaattgaga gcatcactca gcgcatggca ataatagaag gaaagaataa gatggctagc    1560
accttggttg tggctgactc tagaatttct ggaatctaca tttgcatagc ttccaataaa    1620
gttgggactg tgggaagaaa cataagcttt tatatcacag atgtgccaaa tgggtttcat    1680
gttaacttgg aaaaaatgcc gacggaagga gaggacctga actgtcttg cacagttaac    1740 aagttcttat acagagacgt tacttggatt ttactgcgga cagttaataa cagaacaatg    1800
cactacagta ttagcaagca aaaaatggcc atcactaagg agcactccat cactcttaat    1860
cttaccatca tgaatgtttc cctgcaagat tcaggcacct atgcctgcag agccaggaat    1920
gtatacacag gggaagaaat cctccagaag aaagaaatta caatcagagg tgagcactgc    1980
aacaaaaagg ctgttttctc tcggatctcc aaatttaaaa gcacaaggaa tgattgtacc    2040
acacaaagta atgtaaaaca ttaa                                           2064
```

<210> SEQ ID NO 2
<211> LENGTH: 687
<212> TYPE: PRT
<213> ORGANISM: Homo sapiens

<400> SEQUENCE: 2

```
Met Val Ser Tyr Trp Asp Thr Gly Val Leu Leu Cys Ala Leu Leu Ser
1               5                   10                  15

Cys Leu Leu Leu Thr Gly Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240
```

```
Lys Leu Leu Arg Gly His Thr Leu Val Leu Asn Cys Thr Ala Thr Thr
            245                 250                 255
Pro Leu Asn Thr Arg Val Gln Met Thr Trp Ser Tyr Pro Asp Glu Lys
            260                 265                 270
Asn Lys Arg Ala Ser Val Arg Arg Ile Asp Gln Ser Asn Ser His
        275                 280                 285
Ala Asn Ile Phe Tyr Ser Val Leu Thr Ile Asp Lys Met Gln Asn Lys
        290                 295                 300
Asp Lys Gly Leu Tyr Thr Cys Arg Val Arg Ser Gly Pro Ser Phe Lys
305                 310                 315                 320
Ser Val Asn Thr Ser Val His Ile Tyr Asp Lys Ala Phe Ile Thr Val
            325                 330                 335
Lys His Arg Lys Gln Gln Val Leu Glu Thr Val Ala Gly Lys Arg Ser
            340                 345                 350
Tyr Arg Leu Ser Met Lys Val Lys Ala Phe Pro Ser Pro Glu Val Val
            355                 360                 365
Trp Leu Lys Asp Gly Leu Pro Ala Thr Glu Lys Ser Ala Arg Tyr Leu
        370                 375                 380
Thr Arg Gly Tyr Ser Leu Ile Ile Lys Asp Val Thr Glu Glu Asp Ala
385                 390                 395                 400
Gly Asn Tyr Thr Ile Leu Leu Ser Ile Lys Gln Ser Asn Val Phe Lys
            405                 410                 415
Asn Leu Thr Ala Thr Leu Ile Val Asn Val Lys Pro Gln Ile Tyr Glu
            420                 425                 430
Lys Ala Val Ser Ser Phe Pro Asp Pro Ala Leu Tyr Pro Leu Gly Ser
        435                 440                 445
Arg Gln Ile Leu Thr Cys Thr Ala Tyr Gly Ile Pro Gln Pro Thr Ile
        450                 455                 460
Lys Trp Phe Trp His Pro Cys Asn His Asn His Ser Glu Ala Arg Cys
465                 470                 475                 480
Asp Phe Cys Ser Asn Asn Glu Glu Ser Phe Ile Leu Asp Ala Asp Ser
            485                 490                 495
Asn Met Gly Asn Arg Ile Glu Ser Ile Thr Gln Arg Met Ala Ile Ile
            500                 505                 510
Glu Gly Lys Asn Lys Met Ala Ser Thr Leu Val Val Ala Asp Ser Arg
        515                 520                 525
Ile Ser Gly Ile Tyr Ile Cys Ile Ala Ser Asn Lys Val Gly Thr Val
        530                 535                 540
Gly Arg Asn Ile Ser Phe Tyr Ile Thr Asp Val Pro Asn Gly Phe His
545                 550                 555                 560
Val Asn Leu Glu Lys Met Pro Thr Glu Gly Glu Asp Leu Lys Leu Ser
            565                 570                 575
Cys Thr Val Asn Lys Phe Leu Tyr Arg Asp Val Thr Trp Ile Leu Leu
            580                 585                 590
Arg Thr Val Asn Asn Arg Thr Met His Tyr Ser Ile Ser Lys Gln Lys
        595                 600                 605
Met Ala Ile Thr Lys Glu His Ser Ile Thr Leu Asn Leu Thr Ile Met
        610                 615                 620
Asn Val Ser Leu Gln Asp Ser Gly Thr Tyr Ala Cys Arg Ala Arg Asn
625                 630                 635                 640
Val Tyr Thr Gly Glu Glu Ile Leu Gln Lys Lys Glu Ile Thr Ile Arg
            645                 650                 655
```

Gly Glu His Cys Asn Lys Lys Ala Val Phe Ser Arg Ile Ser Lys Phe
            660                 665                 670

Lys Ser Thr Arg Asn Asp Cys Thr Thr Gln Ser Asn Val Lys His
        675                 680                 685

<210> SEQ ID NO 3
<211> LENGTH: 477
<212> TYPE: DNA
<213> ORGANISM: Mus musculus

<400> SEQUENCE: 3

```
atgctggtca tgaagctgtt cacttgcttc ttacaggtcc tagctgggtt ggctgtgcat      60
tcccagggg ccctgtctgc tgggaacaac tcaacagaag tggaagtggt gcctttcaac     120
gaagtgtggg gtcgcagcta ctgtcggccc atggagaagc tggtgtacat cttggatgaa    180
taccctgatg aggtgtctca catattcagt ccgtcctgtg tccttctgag tcgctgtagt    240
ggctgctgtg gtgatgaagg tctgcactgt gtgccgataa agacagccaa catcactatg    300
cagatcttga gattccccc caatcgggat ccacatttct atgtggagat gacattttct    360
caggatgtgc tctgtgaatg cagacctatt ctggagacga caaaggcaga aaggaggaaa    420
accaagggga agaggaagag gagtagaaac tcacagactg aggaaccca cccgtga       477
```

<210> SEQ ID NO 4
<211> LENGTH: 158
<212> TYPE: PRT
<213> ORGANISM: Mus musculus

<400> SEQUENCE: 4

Met Leu Val Met Lys Leu Phe Thr Cys Phe Leu Gln Val Leu Ala Gly
1               5                   10                  15

Leu Ala Val His Ser Gln Gly Ala Leu Ser Ala Gly Asn Asn Ser Thr
            20                  25                  30

Glu Val Glu Val Val Pro Phe Asn Glu Val Trp Gly Arg Ser Tyr Cys
        35                  40                  45

Arg Pro Met Glu Lys Leu Val Tyr Ile Leu Asp Glu Tyr Pro Asp Glu
    50                  55                  60

Val Ser His Ile Phe Ser Pro Ser Cys Val Leu Leu Ser Arg Cys Ser
65                  70                  75                  80

Gly Cys Cys Gly Asp Glu Gly Leu His Cys Val Pro Ile Lys Thr Ala
                85                  90                  95

Asn Ile Thr Met Gln Ile Leu Lys Ile Pro Pro Asn Arg Asp Pro His
            100                 105                 110

Phe Tyr Val Glu Met Thr Phe Ser Gln Asp Val Leu Cys Glu Cys Arg
        115                 120                 125

Pro Ile Leu Glu Thr Thr Lys Ala Glu Arg Arg Lys Thr Lys Gly Lys
    130                 135                 140

Arg Lys Arg Ser Arg Asn Ser Gln Thr Glu Glu Pro His Pro
145                 150                 155

<210> SEQ ID NO 5
<211> LENGTH: 513
<212> TYPE: DNA
<213> ORGANISM: Homo sapiens

<400> SEQUENCE: 5

```
atgccggtca tgaggctgtt cccttgcttc ctgcagctcc tggccgggct ggcgctgcct     60
gctgtgcccc cccagcagtg ggccttgtct gctgggaacg gctcgtcaga ggtggaagtg    120
```

```
gtacccttcc aggaagtgtg gggccgcagc tactgccggg cgctggagag gctggtggac    180
gtcgtgtccg agtacccag  cgaggtggag cacatgttca gcccatcctg tgtctccctg    240
ctgcgctgca ccggctgctg cggcgatgag aatctgcact gtgtgccggt ggagacggcc    300
aatgtcacca tgcagctcct aaagatccgt tctggggacc ggccctccta cgtggagctg    360
acgttctctc agcacgttcg ctgcgaatgc cggcctctgc gggagaagat gaagccggaa    420
aggaggagac ccaagggcag ggggaagagg aggagagaga agcagagacc cacagactgc    480
cacctgtgcg gcgatgctgt tccccggagg taa                                 513
```

<210> SEQ ID NO 6
<211> LENGTH: 170
<212> TYPE: PRT
<213> ORGANISM: Homo sapiens

<400> SEQUENCE: 6

```
Met Pro Val Met Arg Leu Phe Pro Cys Phe Leu Gln Leu Leu Ala Gly
1               5                   10                  15

Leu Ala Leu Pro Ala Val Pro Pro Gln Gln Trp Ala Leu Ser Ala Gly
            20                  25                  30

Asn Gly Ser Ser Glu Val Glu Val Pro Phe Gln Glu Val Trp Gly
        35                  40                  45

Arg Ser Tyr Cys Arg Ala Leu Glu Arg Leu Val Asp Val Val Ser Glu
50                  55                  60

Tyr Pro Ser Glu Val Glu His Met Phe Ser Pro Ser Cys Val Ser Leu
65                  70                  75                  80

Leu Arg Cys Thr Gly Cys Cys Gly Asp Glu Asn Leu His Cys Val Pro
                85                  90                  95

Val Glu Thr Ala Asn Val Thr Met Gln Leu Leu Lys Ile Arg Ser Gly
            100                 105                 110

Asp Arg Pro Ser Tyr Val Glu Leu Thr Phe Ser Gln His Val Arg Cys
        115                 120                 125

Glu Cys Arg Pro Leu Arg Glu Lys Met Lys Pro Glu Arg Arg Arg Pro
130                 135                 140

Lys Gly Arg Gly Lys Arg Arg Glu Lys Gln Arg Pro Thr Asp Cys
145                 150                 155                 160

His Leu Cys Gly Asp Ala Val Pro Arg Arg
                165                 170
```

<210> SEQ ID NO 7
<211> LENGTH: 32
<212> TYPE: DNA
<213> ORGANISM: Artificial
<220> FEATURE:
<223> OTHER INFORMATION: An artificially synthesized primer sequence

<400> SEQUENCE: 7

```
aaggatccgc cgccatggtc agctactggg ac                                  32
```

<210> SEQ ID NO 8
<211> LENGTH: 33
<212> TYPE: DNA
<213> ORGANISM: Artificial
<220> FEATURE:
<223> OTHER INFORMATION: An artificially synthesized primer sequence

<400> SEQUENCE: 8

```
ttctcgagtt aatgttttac attactttgt gtg                                 33
```

<210> SEQ ID NO 9
<211> LENGTH: 35
<212> TYPE: DNA
<213> ORGANISM: Artificial
<220> FEATURE:
<223> OTHER INFORMATION: An artificially synthesized primer sequence

<400> SEQUENCE: 9
aagaattcgc caccatgctg gtcatgaagc tgttc                          35

<210> SEQ ID NO 10
<211> LENGTH: 28
<212> TYPE: DNA
<213> ORGANISM: Artificial
<220> FEATURE:
<223> OTHER INFORMATION: An artificially synthesized primer sequence

<400> SEQUENCE: 10
ttctcgagtc acgggtgggg ttcctcag                                  28

<210> SEQ ID NO 11
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 11
aagtgtgacg ttgacatccg                                           20

<210> SEQ ID NO 12
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 12
gatccacatc tgctggaagg                                           20

<210> SEQ ID NO 13
<211> LENGTH: 23
<212> TYPE: DNA
<213> ORGANISM: Artificial
<220> FEATURE:
<223> OTHER INFORMATION: An artificially synthesized primer sequence

<400> SEQUENCE: 13
ggctgagcat aactaaatct gcc                                       23

<210> SEQ ID NO 14
<211> LENGTH: 24
<212> TYPE: DNA
<213> ORGANISM: Artificial
<220> FEATURE:
<223> OTHER INFORMATION: An artificially synthesized primer sequence

<400> SEQUENCE: 14
ggaatgacga gctcccttcc ttca                                      24

<210> SEQ ID NO 15
<211> LENGTH: 25
<212> TYPE: DNA
<213> ORGANISM: Artificial
<220> FEATURE:

-continued

<223> OTHER INFORMATION: An artificially synthesized primer sequence

<400> SEQUENCE: 15
catccgtaaa gacctctatg ccaac                                    25

<210> SEQ ID NO 16
<211> LENGTH: 19
<212> TYPE: DNA
<213> ORGANISM: Artificial
<220> FEATURE:
<223> OTHER INFORMATION: An artificially synthesized primer sequence

<400> SEQUENCE: 16
atggagccac cgatccaca                                           19

<210> SEQ ID NO 17
<211> LENGTH: 20
<212> TYPE: DNA
<213> ORGANISM: Artificial
<220> FEATURE:
<223> OTHER INFORMATION: An artificially synthesized primer sequence

<400> SEQUENCE: 17
tgctgggaac aactcaacag                                          20

<210> SEQ ID NO 18
<211> LENGTH: 21
<212> TYPE: DNA
<213> ORGANISM: Artificial
<220> FEATURE:
<223> OTHER INFORMATION: An artificially synthesized primer sequence

<400> SEQUENCE: 18
cctcatcagg gtattcatcc a                                        21

<210> SEQ ID NO 19
<211> LENGTH: 69
<212> TYPE: DNA
<213> ORGANISM: Homo sapiens

<400> SEQUENCE: 19
gagctgatca ctctaacatg cacctgtgtg gctgcgactc tcttctggct cctattaacc    60
ctctttatc                                                           69

<210> SEQ ID NO 20
<211> LENGTH: 23
<212> TYPE: PRT
<213> ORGANISM: Homo sapiens

<400> SEQUENCE: 20

Glu Leu Ile Thr Leu Thr Cys Thr Cys Val Ala Ala Thr Leu Phe Trp
1               5                   10                  15

Leu Leu Leu Thr Leu Phe Ile
            20

<210> SEQ ID NO 21
<211> LENGTH: 69
<212> TYPE: DNA
<213> ORGANISM: Mus musculus

<400> SEQUENCE: 21
gagctgatca cgctcacgtg cacatgcgtg gctgcgaccc tcttttggct ccttctaact    60
ctcttcatc                                                           69

```
<210> SEQ ID NO 22
<211> LENGTH: 23
<212> TYPE: PRT
<213> ORGANISM: Mus musculus

<400> SEQUENCE: 22

Glu Leu Ile Thr Leu Thr Cys Thr Cys Val Ala Ala Thr Leu Phe Trp
1               5                   10                  15

Leu Leu Leu Thr Leu Phe Ile
            20
```

MODEL ANIMAL FOR PREGNANCY-INDUCED HYPERTENSION SYNDROME, AND TREATMENT METHOD THEREFOR

TECHNICAL FIELD

The present invention relates to model animals for diseases such as pregnancy-induced hypertension syndrome that shows placenta-specific expression of sFLT1, and methods for producing the model animals. Furthermore, the present invention relates to methods of screening for candidate compounds as therapeutic agents for diseases such as pregnancy-induced hypertension syndrome and pharmaceutical compositions for treating diseases such as pregnancy-induced hypertension syndrome.

BACKGROUND ART

Pregnancy-induced hypertension syndrome arises from placental insufficiency, and is observed in approximately 5 to 7% of pregnant women (Lancet. 2006 Apr. 1; 367(9516): 1066-74, WHO analysis of causes of maternal death: a systematic review (Non-patent Document 1)). Pregnancy-induced hypertension syndrome is a major cause of maternal and infant morbidity and mortality, and the only established therapy is to terminate pregnancy and remove the placenta. Therefore, generating a suitable animal model is extremely significant clinically for understanding the cause of the disease and developing therapeutic agents. Maynard et al. have reported that an increase of soluble FLT1 (sFLT1) and decreases of VEGF and PlGF (placental growth factor, placenta-derived VEGF-like protein) in the mother's blood are observed in women with pregnancy-induced hypertension syndrome (J Clin Invest. 2003 March; 111(5): 649-58, Excess placental soluble fms-like tyrosine kinase 1 (sFlt1) may contribute to endothelial dysfunction, hypertension, and proteinuria in preeclampsia. (Non-patent Document 2)). Since sFLT1 is a soluble form of a VEGF receptor, and antagonizes the functions of VEGF and PlGF, it is considered that sFLT1 causes functional disorders of the vascular endothelium and pregnancy-induced hypertension syndrome due to the impairment of angiogenic signaling (N Engl J. Med. 2004 Feb. 12; 350(7): 672-83. Circulating angiogenic factors and the risk of preeclampsia. (Non-patent Document 3)). This is also supported by the fact that systemic administration of an adenovirus vector (AdV-) that expresses sFLT1 to pregnant rats showed hypertension, proteinuria, and glomerulosclerosis which are classical pathological changes in pregnancy-induced hypertension syndrome (J Clin Invest. 2003 March; 111(5): 649-58, Excess placental soluble fms-like tyrosine kinase 1 (sFlt1) may contribute to endothelial dysfunction, hypertension, and proteinuria in preeclampsia. Long-term maternal cardiovascular function in a mouse model of sFlt-1-induced preeclampsia. (Non-patent Document 2)). However, while sFLT1 is expressed in pregnancy-induced hypertension syndrome until delivery, sFLT1 expression in a model animal was transient. Furthermore, in conventional model animals, since sFLT1 is produced in the mother's body (mainly liver) but not in the placenta which is the causative organ, the pathological condition does not improve upon delivery. That is, the conventional model animals are defective as models for pregnancy-induced hypertension syndrome which shows improvement of pathological conditions upon delivery.

Meanwhile, it has been proven that when blastocyst-stage embryos are infected with a lentiviral vector, genes can be introduced into the placenta alone without being transfected into the mother's body and the unborn baby (Non-patent Documents 4 and 5).

PRIOR ART DOCUMENTS

Patent Documents

[Patent Document 1] WO 2007/020786

Non-Patent Documents

[Non-patent Document 1] Lancet. 2006 Apr. 1; 367(9516): 1066-74, WHO analysis of causes of maternal death: a systematic review

[Non-patent Document 2] J Clin Invest. 2003 March; 111(5): 649-58, Excess placental soluble fms-like tyrosine kinase 1 (sFlt1) may contribute to endothelial dysfunction, hypertension, and proteinuria in preeclampsia.

[Non-patent Document 3] N Engl J. Med. 2004 Feb. 12; 350(7): 672-83. Epub 2004 Feb. 5, Circulating angiogenic factors and the risk of preeclampsia.

[Non-patent Document 4] Nat. Biotechnol. 2007 February; 25(2): 233-7. Complementation of placental defects and embryonic lethality by trophoblast-specific lentiviral gene transfer.

[Non-patent Document 5] Genesis. 2009 December; 47(12): 793-8. Placenta-specific gene activation and inactivation using integrase-defective lentiviral vectors with the Cre/LoxP system.

SUMMARY OF THE INVENTION

Problems to be Solved by the Invention

The present invention was achieved in view of the above circumstances. An objective of the present invention is to provide model animals for diseases such as pregnancy-induced hypertension syndrome which are close to the clinical conditions, and methods for producing the model animals. Another objective of the present invention is to provide methods of screening for candidate compounds as therapeutic agents for diseases such as pregnancy-induced hypertension syndrome, agents for treating diseases such as pregnancy-induced hypertension syndrome, and such using the model animals.

Means for Solving the Problems

To solve the above-mentioned problems, the present inventors aimed to produce non-human animals that express human sFLT1 specifically in the mouse placenta using lentiviral vectors. As a result, the present inventors discovered that the model animals exhibit hypertension, placental insufficiency, intrauterine growth retardation (IUGR), glomerulosclerosis, and proteinuria during pregnancy, and improvement of those symptoms postpartum, which are symptoms very close to the clinical conditions in human.

Furthermore, the present inventors administered pravastatin (PS) to these model animals. As a result, the present inventors discovered that pravastatin induces expression of placenta-derived growth factor (PlGF) which antagonizes sFLT1, and improves symptoms of pregnancy-induced hypertension syndrome, placental insufficiency, intrauterine growth retardation, glomerulosclerosis, and proteinuria caused by sFLT1. Furthermore, the present inventors discovered that pravastatin induces ectopic expression of PlGF in sites other than the placenta.

The present invention is based on such findings, and relates to the following invention:

[1] a non-human mammal that expresses sFLT1 specifically in the placenta;
[2] the non-human mammal of [1], which exhibits symptoms of at least one disease selected from the group consisting of pregnancy-induced hypertension syndrome, placental insufficiency, intrauterine growth retardation, glomerulosclerosis, and proteinuria;
[3] the non-human mammal of [2], which is obtained by the steps of (a) to (c) below:
 (a) removing the zona pellucida of a blastocyst of a non-human mammal;
 (b) introducing an sFLT1-encoding nucleic acid specifically into the trophectoderm of the blastocyst obtained in step (a); and
 (c) transplanting the blastocyst obtained in step (b) into a recipient;
[4] a method of producing a non-human mammal that comprises the steps of (a) to (c) below:
 (a) removing the zona pellucida of a blastocyst of a non-human mammal;
 (b) introducing an sFLT1-encoding nucleic acid specifically into the trophectoderm of the blastocyst obtained in step (a); and
 (c) transplanting the blastocyst obtained in step (b) into a recipient;
[5] a method of screening for a substance that improves the symptoms of pregnancy-induced hypertension syndrome, placental insufficiency, intrauterine growth retardation, glomerulosclerosis, and proteinuria, which comprises the steps of (a) to (c) below:
 (a) obtaining the non-human mammal of any one of [1] to [3];
 (b) administering a test substance to the non-human mammal obtained in step (a); and
 (c) selecting a substance that improves at least one symptom of pregnancy-induced hypertension syndrome, placental insufficiency, intrauterine growth retardation, glomerulosclerosis, and proteinuria, as compared to when the test substance is not administered;
[6] a pharmaceutical composition for use in treating at least one disease selected from the group consisting of pregnancy-induced hypertension syndrome, placental insufficiency, intrauterine growth retardation, glomerulosclerosis, and proteinuria, which comprises a statin as an active ingredient;
[7] a pharmaceutical composition for use in treating at least one disease selected from the group consisting of pregnancy-induced hypertension syndrome, placental insufficiency, intrauterine growth retardation, glomerulosclerosis, and proteinuria, which comprises PlGF or a PlGF-encoding nucleic acid as an active ingredient;
[8] a method for treating at least one disease selected from the group consisting of pregnancy-induced hypertension syndrome, placental insufficiency, intrauterine growth retardation, glomerulosclerosis, and proteinuria, which comprises the step of administering a statin to a subject;
[9] a method for treating at least one disease selected from the group consisting of pregnancy-induced hypertension syndrome, placental insufficiency, intrauterine growth retardation, glomerulosclerosis, and proteinuria, which comprises the step of administering PlGF or a PlGF-encoding nucleic acid to a subject;
[10] use of a statin in the manufacture of a pharmaceutical composition used for treating at least one disease selected from the group consisting of pregnancy-induced hypertension syndrome, placental insufficiency, intrauterine growth retardation, glomerulosclerosis, and proteinuria;
[11] use of PlGF or a PlGF-encoding nucleic acid in the manufacture of a pharmaceutical composition used for treating at least one disease selected from the group consisting of pregnancy-induced hypertension syndrome, placental insufficiency, intrauterine growth retardation, glomerulosclerosis, and proteinuria;
[12] a statin for use in treating at least one disease selected from the group consisting of pregnancy-induced hypertension syndrome, placental insufficiency, intrauterine growth retardation, glomerulosclerosis, and proteinuria;
[13] PlGF or a PlGF-encoding nucleic acid for use in treating at least one disease selected from the group consisting of pregnancy-induced hypertension syndrome, placental insufficiency, intrauterine growth retardation, glomerulosclerosis, and proteinuria;
[14] use of a statin for treating at least one disease selected from the group consisting of pregnancy-induced hypertension syndrome, placental insufficiency, intrauterine growth retardation, glomerulosclerosis, and proteinuria;
[15] use of PlGF or a PlGF-encoding nucleic acid for treating at least one disease selected from the group consisting of pregnancy-induced hypertension syndrome, placental insufficiency, intrauterine growth retardation, glomerulosclerosis, and proteinuria;
[17] an agent for promoting PlGF induction comprising a statin as an active ingredient;
[18] a method for inducing PlGF, which comprises the step of administering a statin to a subject;
[19] use of a statin in the manufacture of a PlGF-inducing agent;
[20] a statin for use in inducing PlGF; and
[21] use of a statin for inducing PlGF.

MODE FOR CARRYING OUT THE INVENTION

Figure 1:
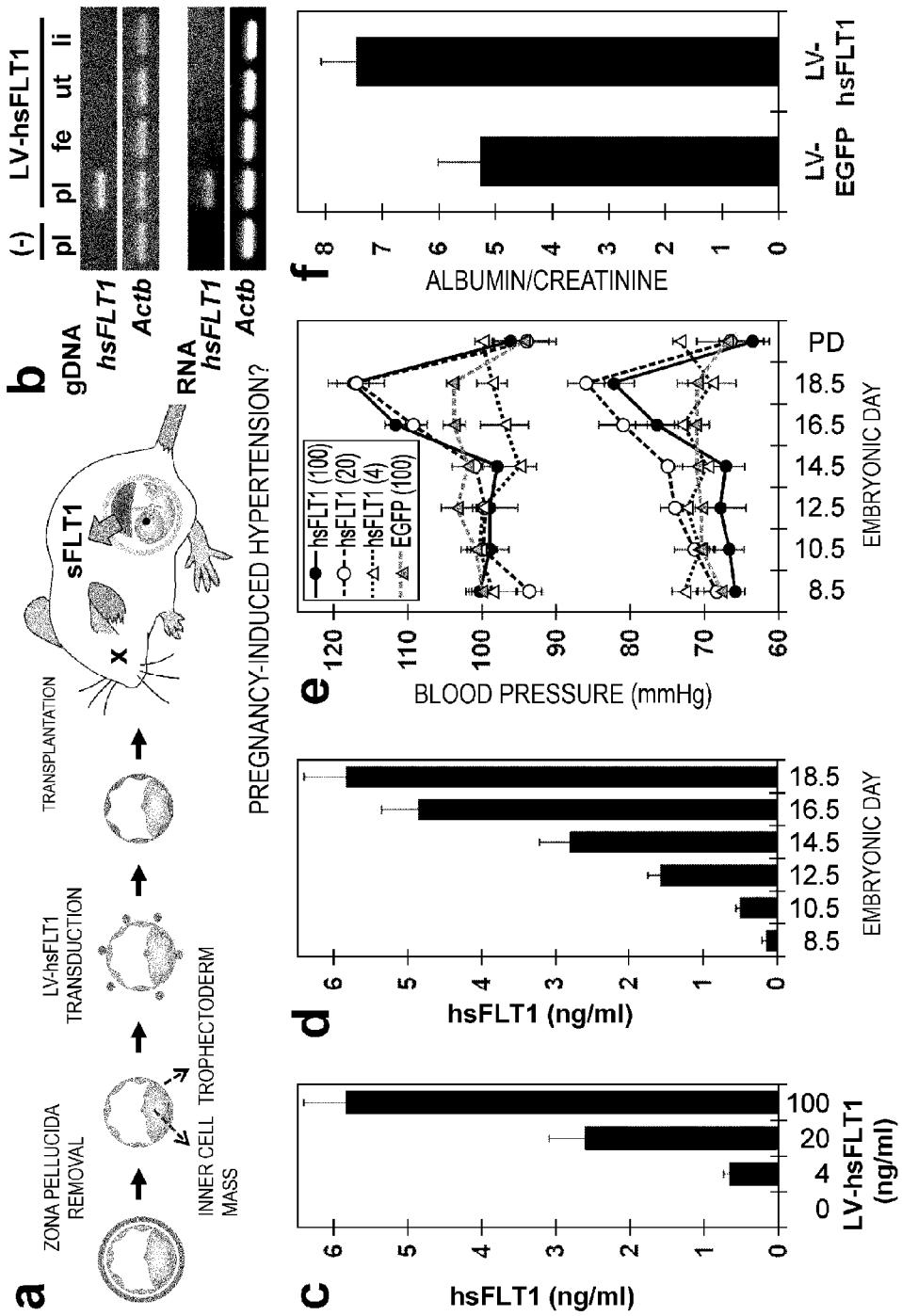
FIG. 1 shows in diagrams and photographs a pregnancy-induced hypertension syndrome model generated by expressing sFLT1 specifically in the placenta. (a) shows a scheme for generating pregnancy-induced hypertension syndrome model mice. After removing the zona pellucida, blastocysts were transduced with a lentiviral vector (LV-hsFLT1) expressing human sFLT1 (hsFLT1) and then transplanted into pseudo-pregnant female animals. The transduced trophectoderm (TE) cell lineage provides the main components of the placenta and continuously expresses hsFLT1. ICM: inner cell mass. (b) Photographs showing the results obtained when genomic DNA (gDNA) and mRNA collected from the indicated tissues at E13.5 were subjected to PCR and RT-PCR, respectively. Actb was used as control. pl: placenta; fe: fetus; ut: uterus; and li: liver. (c-f) Graphs showing results of measuring the hsFLT1 concentration (c and d), blood pressure (e), and ratio of urinary albumin to creatinine (f) in the pregnant female animals. (c) The concentration of hsFLT1 circulating in the mother's blood on the 18th day of pregnancy (at E18.5) depended on the amount of LV-hsFLT1 used for transduction. (d) hsFLT1 circulating in the mother's body increased during pregnancy. (e) Hypertension was observed at E16.5 and E18.5 depending on the amount of LV-hsFLT1. The blood pressure became normal after delivery of the placenta. PD: post-delivery. (f) The ratio of urinary albumin to creatinine was significantly higher in the LV-hsFLT group than in the control LV-EGFP group ($P<0.05$).

The present invention relates to non-human mammals that express soluble fms-like tyrosine kinase-1 (sFLT1) specifically in the placenta. In a preferred embodiment, non-human mammals of the present invention constitutively express sFLT1. In non-human mammals of the present invention, sFLT1 expression is placenta-specific, but placenta-derived sFLT1 circulates in the mother's blood. In the placenta, blood vessels derived from the mother's body and fetus form a very intricate structure (labyrinthine layer) where the blood flows of the mother and the fetus do not mix but gases, hormones, nutrients, and waste are exchanged. Fetus-derived cells are also known to infiltrate into some of the mother's blood vessels. Since sFLT1 produced by fetus-derived cells of the placenta is secreted to the outside of the cells, this is collected through the mother's blood vessels in the placenta, and circulates in the mother's blood via the umbilical cord.

Non-human mammals of the present invention show symptoms of diseases such as pregnancy-induced hypertension syndrome, placental insufficiency, intrauterine growth retardation, glomerulosclerosis, and proteinuria. Furthermore, while sFLT1 expression is placenta-specific, placenta-derived sFLT1 circulates in the mother's blood. In addition, these mammals follow a course very similar to human pathology, such as showing improvement of symptoms of these diseases after delivery. That is, in preferred embodiments, when the non-human mammals of the present invention have placentas, they exhibit symptoms of diseases such as pregnancy-induced hypertension syndrome, placental insufficiency, intrauterine growth retardation, glomerulosclerosis, and proteinuria. When the placenta is taken out from the body at delivery, they demonstrate improvement of symptoms. Such non-human mammals of the present invention are useful as model animals for diseases such as pregnancy-induced hypertension syndrome, placental insufficiency, intrauterine growth retardation, glomerulosclerosis, and proteinuria. Furthermore, non-human mammals of the present invention can be used in methods of screening for candidate compounds as pharmaceutical agents for treating or preventing diseases such as pregnancy-induced hypertension syndrome, placental insufficiency, intrauterine growth retardation, glomerulosclerosis, and proteinuria.

In a preferred embodiment of the present invention, diseases such as pregnancy-induced hypertension syndrome, placental insufficiency, intrauterine growth retardation, glomerulosclerosis, and proteinuria are caused by sFLT1.

FLT1 (membrane-type fms-like tyrosine kinase 1) is a membrane protein known as a specific receptor for vascular endothelial growth factor (VEGF) and placental growth factor (PIGF). On the other hand, sFLT1 (soluble fms-like tyrosine kinase 1) is an FLT1 that does not have a transmembrane domain, and is a soluble protein known as a specific receptor for vascular endothelial growth factor (VEGF) and placental growth factor (PIGF). sFLT1 of the present invention is not limited as long as the whole or a portion of the transmembrane domain is removed from full-length FLT1, and it is soluble and can dimerize. The transmembrane domain can be removed, for example, by protein cleavage, mRNA cleavage, or selective use of exons, without being limited thereto.

The nucleotide sequence and amino acid sequence of the transmembrane domain of human FLT1 identified using SOSUI are shown in SEQ ID NOs: 19 and 20, and the nucleotide sequence and amino acid sequence of the transmembrane domain of mouse FLT1 are shown in SEQ ID NOs: 21 and 22, but the sequences of the transmembrane domain are not limited thereto.

As described, those skilled in the art can easily identify the transmembrane domain in FLT1 derived from various animal species by using a well-known program such as SOSUI.

Furthermore, those skilled in the art can identify the transmembrane domain based on known publications. For example, extracellularly Flt-1 has seven immunoglobulin-like domains: first to seventh; and sFlt-1 is known to have the first to sixth domains among these seven domains, as well as 31 amino acids encoded by the 5' region of intron 13 (Shibuya, Cell Structure and Function, 26, 25-35 (2001)). The 31 amino acids encoded by the 5' region of intron 13 are known to be highly conserved among mammals. Furthermore, the transmembrane domain is encoded by exon 16 of the FLT gene. In fact, it is known that when exon 16 of human FLT1 is deleted, it is converted to a soluble form (Molecular and Cellular Biology, January 2005, p. 346-354, Vol. 25, No. 1, Membrane Fixation of Vascular Endothelial Growth Factor Receptor 1 Ligand-Binding Domain Is Important for Vasculogenesis and Angiogenesis in Mice).

Those skilled in the art can obtain sFLT1 from humans, mice, or other mammals based on such information.

Without being limited thereto, examples of human sFLT1-encoding nucleic acids include the following sequences:
(1) a DNA having the nucleotide sequence (the nucleotide sequence of SEQ ID NO: 1) specified by GenBank: U01134.1; and
(2) a DNA having a nucleotide sequence in which a nucleotide sequence of the transmembrane domain is removed from the nucleotide sequence specified by NCBI Reference Sequence: NM_002019.4.

Furthermore, human sFLT1 proteins include the following sequences but are not limited thereto:
(3) proteins having amino acid sequences encoded by the DNAs of (1) and (2) mentioned above;
(4) a protein having the amino acid sequence (the amino acid sequence of SEQ ID NO: 2) specified by GenBank: U01134.1 and GenBank: AAC50060.1; and
(5) a protein having an amino acid sequence in which an amino acid sequence of the transmembrane domain is removed from the amino acid sequence specified by NCBI Reference Sequence: NP_002010.2.

Furthermore, sFLT1 of the present invention is not limited to human-derived sFLT1. sFLT1 of the present invention include sFLT1 derived from chimpanzees, mice, rats, dogs, cows, horses, pigs, and sheep. These animal-derived sFLT1 also have structures in which the transmembrane domain is removed from full-length FLT1.

Examples of nucleic acids that encode the chimpanzee-derived sFLT1 include nucleic acids having a nucleotide sequence in which a nucleotide sequence of the transmembrane domain is removed from the nucleotide sequence specified by NCBI Reference Sequence: XM_509605.2, but are not limited thereto. Furthermore, examples of chimpanzee-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence XP_509605.2, but are not limited thereto.

Examples of nucleic acids that encode the mouse-derived sFLT1 include a nucleic acid having the nucleotide sequence specified by GenBank: BC029674.1, and nucleic acids having a nucleotide sequence in which a nucleotide sequence of the transmembrane domain is removed from the nucleotide sequence specified by NCBI Reference Sequence: NM_010228.3, but are not limited thereto. Furthermore, examples of mouse-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence NP_034358.2, but are not limited thereto.

Examples of nucleic acids that encode the rat-derived sFLT1 include nucleic acids having a nucleotide sequence in which a nucleotide sequence of the transmembrane domain is removed from the nucleotide sequence specified by NCBI Reference Sequence: NM_019306.1, but are not limited thereto. Furthermore, examples of rat-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence NP_062179.1, but are not limited thereto.

Examples of nucleic acids that encode the dog-derived sFLT1 include nucleic acids having a nucleotide sequence in which a nucleotide sequence of the transmembrane domain is removed from the nucleotide sequence specified by NCBI Reference Sequence: XM_534520.2, but are not limited thereto. Furthermore, examples of dog-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence XP_534520.2, but are not limited thereto.

Examples of nucleic acids that encode the cow-derived sFLT1 include nucleic acids having a nucleotide sequence in which a nucleotide sequence of the transmembrane domain is removed from the nucleotide sequence specified by NCBI Reference Sequence: XM_001249768.2, but are not limited thereto. Furthermore, examples of cow-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence XP_001249768.2, but are not limited thereto.

Examples of nucleic acids that encode the horse-derived sFLT1 include nucleic acids having a nucleotide sequence in which a transmembrane domain nucleotide sequence is removed from the nucleotide sequence specified by NCBI Reference Sequence: XM_001492325.2, but are not limited thereto. Furthermore, examples of horse-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence XP_001492375.1, but are not limited thereto.

Examples of nucleic acids that encode the pig-derived sFLT1 include nucleic acids having a nucleotide sequence in which a nucleotide sequence of the transmembrane domain is removed from the nucleotide sequence specified by NCBI Reference Sequence: XM_001925740.1, but are not limited thereto. Furthermore, examples of pig-derived sFLT1 proteins include proteins having an amino acid sequence encoded by the nucleic acid mentioned above, and proteins having an amino acid sequence in which an amino acid sequence of the transmembrane domain is removed from the amino acid sequence specified by NCBI Reference Sequence XP_001925775.1, but are not limited thereto.

Examples of nucleic acids that encode the sheep-derived sFLT1 include nucleic acids having a nucleotide sequence in which a nucleotide sequence of the transmembrane domain is removed from the nucleotide sequence specified by GenBank: AF233077.1, but are not limited thereto. Furthermore, examples of sheep-derived sFLT1 proteins include proteins having an amino acid sequence encoded by the nucleic acid mentioned above, and proteins having an amino acid sequence in which an amino acid sequence of the transmembrane domain is removed from the amino acid sequence specified by GenBank: AAF60281.1, but are not limited thereto.

In the present invention, "nucleic acids encoding sFLT1" include "sFLT1-encoding DNAs" and "sFLT1-encoding RNAs".

In the present invention, "pregnancy-induced hypertension syndrome" refers to observation of either hypertension or hypertension accompanied by proteinuria after the 20th week of pregnancy and until 12 weeks postpartum, and these symptoms are not simply due to incidental complications of pregnancy. Progression of pregnancy-induced hypertension syndrome leads to placental insufficiency, intrauterine growth retardation, glomerulosclerosis, and proteinuria.

A non-human mammal of the present invention that shows placenta-specific expression of sFLT1 can be produced by the steps of (a) to (c) below:
(a) removing the zona pellucida of a blastocyst of a non-human mammal;
(b) introducing an sFLT1-encoding nucleic acid specifically into the trophectoderm of the blastocyst obtained in step (a); and
(c) transplanting the blastocyst obtained in step (b) into a recipient.

In the present invention, the recipient is preferably a non-human mammal.

Non-human animals obtained by such steps exhibit symptoms of diseases such as pregnancy-induced hypertension syndrome, placental insufficiency, intrauterine growth retardation, glomerulosclerosis, and proteinuria.

First, in the production of non-human mammals of the present invention, blastocysts are obtained. A blastocyst refers to an embryo that has completed the cleavage stage in the early development of mammals. Mammalian eggs are alecithal; and they divide holoblastically and form aggregates of blastomeres. At the 32-cell stage, eggs divide into inner cell mass inside the aggregate and trophectoderm which enfolds the outside of the aggregate. The inner cell mass develops into the body of a fetus in the future, while the trophectoderm differentiates into the placenta in the future. In the methods of the present invention, sFLT1-encoding nucleic acids are introduced specifically into trophectodermal cells that form the outermost layer of a blastocyst.

Animals from which the blastocysts are derived include non-human animals. Examples of non-human animals include humans, mice, rats, rabbits, guinea pigs, hamsters, dogs, cats, cows, horses, pigs, goats, and sheep, but are not particularly limited thereto.

Blastocysts can be prepared by the methods described below. For example, eggs and sperms are collected from any non-human mammals, and then fertilization is carried out by methods known to those skilled in the art. Blastocysts can be prepared from the resulting fertilized eggs by methods known to those skilled in the art, for example, by culturing eggs in a kSOM medium for 96 hours. Alternatively, blastocysts may be obtained directly from animals according to methods that are conventionally used by those skilled in the art (for example, methods described in: Manipulating the mouse embryo, a laboratory manual, 3rd edition, p201-203, Cold Spring Harbor Laboratory Press).

In the non-human mammal production of the present invention, the zona pellucida is then removed from the blastocysts obtained above. Embryos (preimplantation early embryos) are covered with zona pellucida, which is an extracellular matrix, to protect them from infection of viruses or the like. In the present invention, the zona pellucida is removed.

The zona pellucida can be removed by known methods, for example, acid treatment, enzyme treatment, or physical treatment. One example of such acid treatment is a treatment that uses acidic Tyrode's solution (Manipulating the mouse embryo, a laboratory manual, 3rd edition, p485-486, Cold Spring Harbor Laboratory Press). The zona pellucida is partially dissolved, for example, by sucking acidic Tyrode's solution (pH 2.3 to 2.5) with a micropipette and then gently spraying immobilized embryos with the solution. Alternatively, the zona pellucida is dissolved by immersing embryos in acidic Tyrode's solution.

Enzyme treatment for removal of zona pellucida includes Pronase treatment (Calbiochem 537088, Sigma P5147) and the like. For example, embryos are placed in a solution of 0.5% Pronase until the zona pellucida dissolves. After the zona pellucida dissolves, the embryos are washed well with a medium, and then zona pellucida-removed blastocysts can be obtained (Manipulating the mouse embryo, a laboratory manual, 3rd edition, p731, Cold Spring Harbor Laboratory Press).

Furthermore, in the present invention, zona pellucida may also be removed by physical methods. Such physical methods of removal include a zona pellucida dissection method in which embryos are immobilized and part of the zona pellucida is dissected with a micropipette (Hum. Reprod., 5: 7-13, 1990), methods for dissecting, drilling, or thinning zona pellucida with a laser (Hum. Reprod., 15: 1061-1064, 2000) or piezomicromanipulator (Developmental Biology, 250: 348-357, 2002) and the like.

Zona pellucida can be removed by the methods described above. In the present invention, however, methods for removing zona pellucida are not limited to the examples described above, and the methods include all methods that can remove zona pellucida.

In the non-human mammal production of the present invention, sFLT1-encoding nucleic acids are then introduced into zona pellucida-removed blastocysts. In a preferred embodiment, methods for introducing sFLT1-encoding nucleic acids into zona pellucida-removed blastocysts include methods for introducing a vector carrying an sFLT1-encoding nucleic acid into blastocysts, but are not particularly limited thereto.

Vectors carrying an sFLT1-encoding nucleic acid to be introduced into blastocysts include viral vectors. Viral vectors include DNA viral vectors and RNA viral vectors. DNA viral vectors include adenovirus vectors, adeno-associated virus vectors, and such, but are not limited thereto. Furthermore, RNA viral vectors include retroviral vectors (Molecular Therapy 2003, 8; 666-673) such as lentiviral vectors (Molecular Therapy 2003, 8: 666-673). Furthermore, as described later, reagents for introducing nucleic acids such as HVJ liposomes, Lipofectamine, and such can also be used. HVJ (hemagglutinating virus of Japan: Sendai virus)-liposome is a vector that can efficiently introduce liposome-encapsulated genes and oligonucleotides into various organs in a living body, by using the DNA-binding protein HMG-1 and the activity of a fusion protein of HVJ which is a virus that causes cell fusion.

Of such vectors, lentiviral vectors are preferred. Lentivirus belongs to the retrovirus family, and is an immunodeficiency virus in human, monkey, cat, and bovine. With respect to gene structure, the virus is constituted by several regulatory genes in addition to structural genes fundamental to the retrovirus (gag, pol, and env). Lentiviral vectors constructed by altering the lentivirus can integrate foreign genes into chromosome, and thus long term expression of the genes introduced therein can be expected. Furthermore, unlike other retroviral vectors, lentiviral vectors have a nuclear translocation signal, and thus can introduce genes into non-dividing cells.

Lentiviral vectors used in the present invention include all lentiviral vectors having at least LTR, RRE, and GAG Lentiviral vectors used in the non-human mammal production of the present invention should have at least these requirements, but may additionally have other genes, for example, deltaU3, PPT, and WPRE. Such lentiviral vectors are also preferably used as the viral vector in the methods of the present invention.

In a particularly preferred embodiment, lentiviral vectors used in the present invention have LTR (deltaU3), GAG, RRE, PPT, and WPRE. A representative example of lentiviral vectors having such structures is a vector constructed by substituting a cDNA of interest for the GFP moiety of the GFP viral vector disclosed in the following document: Molecular Therapy 2003, 8: 666-673. The vector structure and construction method are disclosed in the document indicated above.

In the present invention, the timing and amount of the sFLT1-encoding nucleic acid introduced into blastocysts are not particularly limited. However, preferably it is introduced at a quantity and timing that leads to presentation of symptoms of pregnancy-induced hypertension syndrome in a recipient transplanted with the sFLT1-introduced blastocysts. The dose is preferably 10 to 1,000 ng-p24/mL, more preferably 20 to 500 ng-p24/mL, and even more preferably 100 to 500 ng-p24/mL, but is not limited thereto. Furthermore, the timing of introducing the sFLT1-encoding nucleic acid into blastocysts is preferably before implantation.

Blastocysts can be infected with a lentiviral vector carrying an sFLT1-encoding nucleic acid, for example, by mixing zona pellucida-removed blastocysts with a solution containing the lentiviral vector carrying the sFLT1-encoding nucleic acid, and then leaving the mixture to stand for 4 to 5 hours. By this method, a lentiviral vector carrying an sFLT1-encoding nucleic acid can be specifically introduced into the trophectoderm.

Alternatively, sFLT1-encoding nucleic acids may also be introduced into zona pellucida-removed blastocysts by using a nucleic acid transfection reagent. Herein, the nucleic acid transfection reagent refers to any reagent that can introduce an sFLT1-encoding nucleic acid into blastocysts. Such nucleic acid transfection reagents include, but are not limited to, for example, Lipofectoamine 2000 (Invitrogen), Effectene (Qiagen), and FuGene (Roche).

Herein, an sFLT1-encoding nucleic acid includes sFLT1-encoding DNA and sFLT1-encoding RNA, but is not limited thereto. An sFLT1-encoding nucleic acid to be introduced may be in a form such as DNA, RNA, cDNA, mRNA, or artificial nucleic acid. Such DNAs, RNAs, cDNAs, and mRNAs also include derivatives thereof. Such artificial nucleic acids include, but are not limited to, for example, DNAs, RNAs, cDNAs, mRNAs with modified sugar chain structures, or derivatives thereof. Furthermore, sFLT1-encoding nucleic acids to be introduced may be naked DNAs or polynucleotides introduced into a vector. Those skilled in the art can design and use appropriate vectors depending on the purpose. Vectors used in the present invention may comprise, in addition to an sFLT1-encoding nucleic acid to be introduced, polynucleotide regions that function in expression hosts, such as transcriptional initiation site and transcription termination site, for more efficient expression of the sFLT1-encoding nucleic acid.

Those skilled in the art can readily obtain sFLT1-endocing nucleic acids. For example, such polynucleotides can be isolated from natural sources, using various biological samples such as placental tissues, trophoblast stem cells, and differentiated cells thereof as a source, based on their physicochemical properties and the like. Alternatively, the polynucleotides may be chemically synthesized based on known sequence information.

sFLT1-encoding nucleic acids include homologous genes from various animals. Herein, "homologous gene" refers to the above-listed polynucleotide comprising a nucleotide sequence of SEQ ID NO: 1, or polynucleotides encoding a protein having a biological function equivalent to that of the transcription/translation products of such polynucleotides, in various animals.

Methods that are well known to those skilled in the art for isolating homologous genes include hybridization techniques (Southern, E. M., Journal of Molecular Biology, Vol. 98, 503, 1975) and polymerase chain reaction (PCR) techniques (Saiki, R. K., et al. Science, vol. 230, 1350-1354, 1985; Saiki, R. K. et al. Science, vol. 239, 487-491, 1988). More specifically, those skilled in the art can routinely isolate sFLT1-encoding polynucleotides from various animal cells and tissues (for example, placental tissues, trophoblast stem cells, and differentiated cells thereof), using as a probe, polynucleotides encoding sFLT1 (for example, the nucleotide sequence of SEQ ID NO: 1) or a portion thereof, or using as a primer, oligonucleotides that specifically hybridize to the sFLT1-encoding polynucleotides. Alternatively, sequences of homologous genes may be obtained from known databases.

In order to isolate nucleic acids encoding such homologous genes, the hybridization reaction is usually performed under stringent conditions. Those skilled in the art can appropriately select stringent hybridization conditions. For example, hybridization may be performed by pre-hybridizing overnight at 42° C. in a hybridization solution containing 25% formamide, or 50% formamide under more stringent conditions; 4×SSC; 50 mM Hepes, pH 7.0; 10×Denhardt's solution; and 20 µg/mL denatured salmon sperm DNA, then adding a labeled probe, and then incubating the solution overnight at 42° C. The subsequent washes can be carried out using a washing solution and temperature condition of "1×SSC, 0.1% SDS, 37° C." or such, "0.5×SSC, 0.1% SDS, 42° C." or such for more stringent conditions, or "0.2×SSC, 0.1% SDS, 65° C." or such for even more stringent conditions. With more stringent washing conditions for hybridization such as these, isolation of a DNA with higher homology to the probe sequence can be expected. However, the above-mentioned combinations of SSC, SDS, and temperature conditions are examples, and those skilled in the art can suitably combine the above-mentioned factors or with other factors (for example, probe concentration, probe length, hybridization reaction time, etc.) that determine hybridization stringency to achieve similar stringency.

Isolation of DNAs with higher homologies can be expected under conditions of higher stringency such as conditions of 6 M urea, 0.4% SDS, and 0.1×SSC. High homology refers to sequence identities of at least 50% or more, preferably 70% or more, more preferably 90% or more, and most preferably 95% or more of the whole amino acid sequence. The number of amino acids to be altered in a mutant is generally 30 amino acids or less, preferably 15 amino acids or less, more preferably 5 amino acids or less, even more preferably 3 amino acids or less, and yet even more preferably 2 amino acids or less.

The BLAST algorithm by Karlin and Altschul (Proc. Natl. Acad. Sci. USA 87: 2264-2268, 1990; Proc. Natl. Acad. Sci. USA 90: 5873, 1993) can be used to determine the amino acid sequence identity and nucleotide sequence identity.

sFLT1-encoding polynucleotides of the present invention are not particularly limited, but include preferably polynucleotides derived from humans, mice, rats, rabbits, guinea pigs, hamsters, dogs, cats, cows, horses, pigs, goats, and sheep, and particularly preferably polynucleotides derived from human.

In the methods of the present invention for producing non-human animals, the above blastocysts are finally transplanted into a recipient. In the present invention, the recipient is preferably a non-human animal. The recipient is preferably the same animal or an animal belonging to the same species as the animal from which the blastocysts are derived. Those skilled in the art can routinely transplant blastocysts into recipients (Manipulating the mouse embryo, a laboratory manual, 3rd edition, p 263-271, Cold Spring Harbor Laboratory Press; Bovine Embryo Transplantation (Ushi no Hai Ishoku), Hafez, Theriogenology (Kachiku Hanshokugaku), 5th edition, translation supervisors: S. Yoshida, J. Masaki, A. Iritani, Nishimura Shoten, 1992). Non-human animals to be produced in the present invention include, for example, mice, rats, rabbits, guinea pigs, hamsters, dogs, cats, cows, horses, pigs, goats, and sheep, but are not particularly limited thereto.

It is possible to determine whether an sFLT1-encoding nucleic acid has been introduced specifically into the trophectoderm of a blastocyst by the methods of the present invention, by using methods known to those skilled in the art, for example, by amplifying introduced genes with PCR, or by detecting the expression of reporter genes such as EGFP or lacZ with a fluorescence or coloring method.

The present invention relates to methods for producing non-human mammals that show placenta-specific expression of sFLT1 including such steps. Furthermore, the present invention relates to methods for producing blastocysts in which an sFLT1-encoding nucleic acid is introduced specifically into the trophectoderm.

The present invention also relates to a method of screening for a substance that improves the symptoms of at least one disease selected from the group consisting of pregnancy-induced hypertension syndrome, placental insufficiency, intrauterine growth retardation, glomerulosclerosis, and proteinuria, which comprises the steps of (a) to (c) below:
(a) obtaining a non-human mammal that shows placenta-specific expression of sFLT1 described herein;
(b) administering a test substance to the non-human mammal obtained in step (a); and
(c) selecting a substance that improves the symptoms of at least one disease selected from the group consisting of pregnancy-induced hypertension syndrome, placental insufficiency, intrauterine growth retardation, glomerulosclerosis, and proteinuria, as compared to when the test substance is not administered.

Substances obtained by screening methods of the present invention may become candidate compounds as therapeutic agents for at least one disease selected from the group consisting of pregnancy-induced hypertension syndrome, placental insufficiency, intrauterine growth retardation, glomerulosclerosis, and proteinuria. Therefore, "methods of screening for substances that improve the symptoms of at least one disease selected from the group consisting of pregnancy-induced hypertension syndrome, placental insufficiency, intrauterine growth retardation, glomerulosclerosis, and proteinuria" can also be described as methods of screening for candidate compounds as therapeutic agents for at least one disease selected from the group consisting of pregnancy-induced hypertension syndrome, placental insufficiency, intrauterine growth retardation, glomerulosclerosis, and proteinuria.

In the screening method of the present invention, first, a non-human mammal that shows placenta-specific expression of sFLT1 described herein is obtained. Such a non-human mammal can be obtained by the above-described method.

Next, a test substance is administered to the non-human mammal that shows placenta-specific sFLT1 expression of the present invention. Test substances include, for example, single compounds such as natural compounds, organic compounds, inorganic compounds, proteins, and peptides, as well as compound libraries, expression products of gene libraries, cell extracts, cell culture supernatants, microbial fermentation products, marine organism extracts, and plant extracts, but are not limited thereto.

Administration of a test compound to a non-human mammal of the present invention that shows placenta-specific expression of sFLT1 can be carried out, for example, orally or parenterally, but is not limited thereto. When a test compound is a protein, for example, a viral vector carrying a gene that encodes the protein is constructed, and the gene can be introduced into the genetically-modified non-human mammal of the present invention utilizing the infectivity of the viral vector.

In a screening method of the present invention, the last step is to determine whether the symptoms of at least one disease selected from the group consisting of pregnancy-induced hypertension syndrome, placental insufficiency, intrauterine growth retardation, glomerulosclerosis, and proteinuria are improved by the test substance. Then, substances that improve the symptoms of at least one disease selected from the group consisting of pregnancy-induced hypertension syndrome, placental insufficiency, intrauterine growth retardation, glomerulosclerosis, and proteinuria, as compared to when the test substance is not administered, are selected. For example, when the level of PlGF mRNA in placenta or the PlGF concentration in the mother's blood is increased, it is determined that the test substance improves the symptoms of at least one disease selected from the group consisting of pregnancy-induced hypertension syndrome, placental insufficiency, intrauterine growth retardation, glomerulosclerosis, and proteinuria. The level of PlGF mRNA can be measured by Northern blotting, quantitative RT-PCR, microarray analysis, and such. Furthermore, the blood concentration can be measured by Western blotting or ELISA.

Alternatively, blood pressure is measured or albumin/creatinine in urine is measured, and when these values decrease, the test substance is judged to have improved symptoms of pregnancy-induced hypertension syndrome. Furthermore, it is judged that the test substance improves symptoms in cases of glomerulosclerosis improvement when pathological sections of the kidney are observed, angioplasia improvement when pathological sections of a placenta are observed, or recovery of decreased weight of the fetus and placenta.

Furthermore, the present invention relates to a pharmaceutical composition (therapeutic agent) for treating at least one disease selected from the group consisting of pregnancy-induced hypertension syndrome, placental insufficiency, intrauterine growth retardation, glomerulosclerosis, and proteinuria, comprising a statin as an active ingredient. The present invention also provides a pharmaceutical composition (therapeutic agent) for treating at least one disease selected from the group consisting of pregnancy-induced hypertension syndrome, placental insufficiency, intrauterine growth retardation, glomerulosclerosis, and proteinuria, comprising a placental growth factor (PlGF) or a PlGF-encoding nucleic acid as an active ingredient.

The present inventors have confirmed that symptoms of pregnancy-induced hypertension syndrome, placental insufficiency, intrauterine growth retardation, glomerulosclerosis, and proteinuria improve as a result of administering a statin, known as a therapeutic agent for hyperlipidemia, to the non-human model mammal developed by the present inventors. Furthermore, they confirmed that PlGF expression is induced by statin administration. Accordingly, statins, PlGF, and PlGF-encoding nucleic acids (DNA, RNA) may be useful as therapeutic agents for pregnancy-induced hypertension syndrome, placental insufficiency, intrauterine growth retardation, glomerulosclerosis, and proteinuria.

Statins have the following effects in humans and non-human animals in which sFLT1 is specifically introduced into the placenta:
significantly reduces the concentration of sFLT1 in the mother's blood;
does not affect the concentration of VEGF in the mother's blood;
significantly induces the level of PlGF mRNA and increases the level by approximately five-fold particularly in the placenta;
significantly induces the concentration of PlGF in the mother's blood;
ameliorates placental formation disorder;
ameliorates intrauterine growth restriction;
improves hypertension; and
improves renal dysfunction.

Furthermore, statins significantly increase circulating PlGF in wild-type pregnant female animals and non-pregnant animals. Furthermore, they do not lower blood pressure in normal pregnant female animals.

Pravastatin and atorvastatin induce PlGF production in human umbilical vein endothelial cells (HUVEC).

Furthermore, PlGF has the following effects in non-human animals in which sFLT1 is introduced specifically into the placenta:
improves hypertension by impairing sFLT1 in the mother's blood;
improves renal dysfunction;
ameliorates placental formation disorder; and
ameliorates intrauterine growth restriction.

Statin (HMG-CoA reductase inhibitor) is a general term for substances that reduce the blood cholesterol level by inhibiting the function of HMG-CoA reductase. Known statins include:
Mevastatin (synonym: compactin; chemical name: [(1S,7S,8S,8aR)-842-[(2R,4R)-4-hydroxy-6-oxooxan-2-yl)ethyl]-7-methyl-1,2,3,7,8,8a-hexahydronaphthalen-1-yl] (2S)-2-methylbutanoate, [(1S,7S,8S,8aR)-8-[2-[(2R,4R)-4-hydroxy-6-oxooxan-2-yl]ethyl]-7-methyl-1,2,4a,7,8,8a-hexahydronaphthalen-1-yl](2S)-2-methylbutanoate, [8-[2-(4-hydroxy-6-oxooxan-2-yl)ethyl]-7-methyl-1,2,3,7,8,8a-hexahydronaphthalen-1-yl]2-methylbutanoate, etc.);
Atorvastatin (chemical name: (−)-Monocalcium bis{(3R,5R)-7-[2-(4-fluorophenyl-5-isopropyl-3-phenyl-4-phenylcarbamoyl-1H-pyrrol-1-yl]-3,5-dihydroxyheptanoate}trihydrate, etc.);
Simvastatin (chemical name: (1S,3R,7S,8S,8aR)-8-[2-[(2R,4R)-4-Hydroxy-6-oxotetrahydro-2H-pyran-2-yl]-ethyl]-3,7-dimethyl-1,2,3,7,8,8a-hexahydronaphthalen-1-yl 2,2-dimethylbutanoate, etc.);
Cerivastatin (chemical name: (E,3R,5S)-7-[4-(4-fluorophenyl)-5-(methoxymethyl)-2,6-di(propan-2-yl)pyridin-3-yl]-3,5-dihydroxyhept-6-enoic acid, etc.);
Pitavastatin (chemical name: (+)-monocalcium bis{(3R,5S,6E)-7-[2-cyclopropyl-4-(4-fluorophenyl)-3-quinolyl]-3,5-dihydroxy-6-heptenoate}, etc.);
Pravastatin (chemical name: Monosodium(3R,5R)-3,5-dihydroxy-7-{(1S,2S,6S,8S,8aR)-6-hydroxy-2-methyl-8-[(2S)-2-methylbutanoyloxy]-1,2,6,7,8,8a-hexahydronaphthalen-1-yl}heptanoate);
Fluvastatin (chemical name: (±)-(3RS,5SR,6E)-Sodium-7-[3-(4-fluorophenyl)-1-(1-methylethyl)-1H-indol-2-yl]-3,5-dihydroxy-6-heptenoate, etc.);
Rosuvastatin (chemical name: Monocalcium bis((3R,5S,6E)-7-{4-(4-fluorophenyl)-6-isopropyl-2-[methanesulfonyl(methyl)amino]pyrimidin-5-yl}-3,5-dihydroxyhept-6-enoate), etc.); and
Lovastatin (chemical name: R1S,3R,7S,8S,8aR)-8-[2-[(2R,4R)-4-hydroxy-6-oxooxan-2-yl)ethyl]-3,7-dimethyl-1,2,3,7,8,8a-hexahydronaphthalen-1-yl](2S)-2-methylbutanoate), etc.).

Those skilled in the art can synthesize statins besides mevastatin according to the description in Japanese Patent Kohyo Publication No. (JP-A) 2009-538831 (unexamined Japanese national phase publication corresponding to a non-Japanese international publication). Furthermore, those skilled in the art can obtain mevastatin, for example, by the method described in the Journal of Lipid Research, Volume 33, 1992. Alternatively, pravastatin and atorvastatin can be purchased from Cayman Chemical and Toronto Research Chemicals, respectively. Furthermore, they can be obtained from many pharmaceutical companies as prescription drugs.

The PlGF genes and proteins encoded by these genes are known. For example, a mouse PlGF gene and a protein encoded by the gene are known as GenBank: BC016567.1, and a human PlGF gene and a protein encoded by the gene are known as GenBank: BC001422.2. The nucleotide sequence of the mouse PlGF gene is shown in SEQ ID NO: 3, and the protein encoded by the gene is shown in SEQ ID NO: 4. The nucleotide sequence of the human PlGF gene is shown in SEQ ID NO: 5, and the protein encoded by the gene is shown in SEQ ID NO: 6.

PlGF genes and proteins encoded by these genes are also known for chimpanzees, rats, dogs, cows, horses, pigs, sheep, and such. The respective accession numbers are shown below.
NCBI Reference Sequence

| chimpanzee | gene XM_001158223.1 | protein XP_001158223.1 |
| rat | gene NM_053595.2 | protein NP_446047.1 |
| dog | gene XM_849639.1 | protein XP_854732.1 |
| cow | gene NM_173950.2 | protein NP_776375.1 |
| horse | gene XM_001491442.1 | protein XP_001491492.1 |
| Genbank | | |
| pig | gene FJ177137.1 | protein ACI24003.1 |
| sheep | gene AY157708.1 | protein AAN77495.1 |

"PlGF-encoding nucleic acids" in the pharmaceutical agents of the present invention include "PlGF-encoding DNA" and "PlGF-encoding RNA". The form of "PlGF-encoding DNA" is not particularly limited, and may be a genomic DNA, cDNA, synthetic DNA, or vector containing such DNA.

Furthermore, in addition to as a naturally-occurring protein, "PlGF" in a pharmaceutical composition (therapeutic agent) of the present invention can be prepared as a recombinant protein using known genetic engineering techniques. In addition, the organism from which "PlGF" in a pharmaceutical composition (therapeutic agent) of the present invention is derived is not particularly limited. When it is used for treatment or prevention of human diseases, it is preferably derived from a mammal, and most preferably derived from a human. The naturally-occurring protein can be prepared, for example, by affinity chromatography methods that utilize antibodies against PlGF in tissue extracts such as the placenta which is believed to express PlGF.

On the other hand, recombinant proteins can be prepared, for example, as a recombinant polypeptide by methods known to those skilled in the art. Recombinant polypeptides can be prepared, for example, by inserting a PlGF-encoding nucleic acid into a suitable expression vector, collecting transformants obtained by introducing this vector into suitable host cells, and after obtaining an extract thereof, purifying it by chromatography such as ion exchange, reverse phase, or gel filtration, or by affinity chromatography in which antibodies against PlGF are immobilized onto the column, or by combining a plurality of such columns Alternatively, when PlGF is expressed as a fusion polypeptide with a glutathione S-transferase protein, or as a recombinant polypeptide with multiple additions of histidines in host cells (for example, an animal cell or *Escherichia coli*), the expressed recombinant polypeptide can be purified using a glutathione column or a nickel column With regard to the above vectors, for example, when the host is *E. coli*, as long as the vector has an "ori" for amplification in *E. coli* such that the vector is amplified and prepared in large quantities in *E. coli* (for example, JM109, DH5α, HB101, and XL1Blue) or such, and further has a selection gene for transformed *E. coli* (for example, a drug resistance gene that allows differentiation using a certain drug (ampicillin, tetracycline, kanamycin, or chloramphenicol)), the vectors are not particularly limited. The vectors include, for example, M13 vectors, pUC vectors, pBR322, pBluescript, and pCR-Script. In addition to the above vectors, for example, pGEM-T, pDIRECT, and pT7 can also be used for the subcloning and excision of cDNAs. When using vectors to produce PlGF, expression vectors are particularly useful. When an expression vector is expressed in *E. coli*, for example, it should have the above characteristics in order to be amplified in *E. coli*. Additionally, when *E. coli* such as JM109, DH5α, HB101, or XL1-Blue are used as the host, the vector must have a promoter that allows efficient expression in *E. coli*, for example, a lacZ promoter (Ward et al. Nature 341: 544-546, 1989; FASEB J. 6: 2422-2427, 1992), araB promoter (Better et al. Science 240: 1041-1043, 1988), or T7 promoter. Other examples of the vectors include pGEX-5X-1 (Pharmacia), "QIAexpress system" (QIAGEN), pEGFP, and pET.

Furthermore, the vector may comprise a signal sequence for polypeptide secretion. When producing polypeptides into the periplasm of *E. coli*, the pelB signal sequence (Lei, S. P. et al. J. Bacteriol. 169: 4379 (1987)) may be used as a signal sequence for polypeptide secretion. For example, calcium chloride methods or electroporation methods may be used to introduce the vector into a host cell.

In addition to *E. coli*, expression vectors derived from mammals (e.g., pcDNA3 (Invitrogen), pEGF-BOS (Nucleic Acids Res. 18(17): 5322 (1990)), pEF, and pCDM8), insect cells (e.g., "Bac-to-BAC baculovirus expression system" (GIBCO-BRL) and pBacPAK8), plants (e.g., pMH1 and pMH2), animal viruses (e.g., pHSV, pMV, and pAdexLcw), retroviruses (e.g., pZIPneo), yeasts (e.g., "*Pichia* Expression Kit" (Invitrogen), pNV11 and SP-Q01), and *Bacillus subtilis* (e.g., pPL608 and pKTHSO) may also be used as vectors for producing PlGF.

For expression in animal cells such as CHO, COS, and NIH3T3 cells, the vector must have a promoter necessary for expression in such cells, for example, an SV40 promoter (Mulligan et al. Nature 277: 108 (1979)), MMLV-LTR promoter, EF1α promoter (Mizushima et al. Nucleic Acids Res. 18: 5322 (1990)), or CMV promoter. It is even more preferable that the vector comprises a gene for selecting transformants (for example, a drug-resistance gene enabling differentiation by a drug (such as neomycin and G418)). Examples of vectors with such characteristics include pMAM, pDR2, pBK-RSV, pBK-CMV, pOPRSV, and pOP13.

On the other hand, in vivo polypeptide production systems include those using animals or plants. A PlGF-encoding nucleic acid is introduced into the animals or plants to produce PlGF in the body of the animals or plants, and polypeptides are collected from them.

Production systems using animals include those that use mammals or insects. Mammals that can be used include goats, pigs, sheep, mice, cows and such (Vicki Glaser, SPECTRUM Biotechnology Applications, 1993). When mammals are used, transgenic animals can be used.

For example, nucleic acid encoding PlGF can be prepared as a fusion gene with a gene encoding a polypeptide such as goat β casein which is uniquely produced into milk. Next, DNA fragments comprising the fusion gene are injected into goat embryos, and the embryos are introduced into female goats. PlGF can be obtained from milk produced by the transgenic animals born to the goats that received the embryos, or produced from progenies of these animals. The transgenic goats can be given hormones to increase the volume of milk containing the polypeptide that they produce (Ebert, K. M. et al., Bio/Technology (1994) 12, 699-702).

As insects, for example, silkworms can be used. When silkworms are used, PlGF is obtained from the body fluids of silkworms (Susumu, M. et al., Nature (1985) 315, 592-594) after the silkworms are infected with a baculovirus into which a nucleic acid encoding PlGF has been inserted.

Moreover, when plant is used, for example, tobacco can be used. When tobacco is used, a nucleic acid encoding PlGF is inserted into a plant expression vector (e.g., pMON 530) and the vector is introduced into bacteria such as *Agrobacterium tumefaciens*. This bacterium is used to infect tobacco (e.g., *Nicotiana tabacum*) such that PlGF can be obtained from the leaves of this tobacco (Julian K.-C. Ma et al., Eur. J. Immunol. (1994) 24, 131-138).

The resulting PlGF may be isolated from the inside or outside (such as medium) of host cells, and purified as substantially pure and homogenous polypeptides. Methods for isolation and purification commonly used for polypeptide purification may be used for the isolation and purification of polypeptides, and they are not limited to any method. Polypeptides may be isolated and purified by appropriately selecting and combining, for example, column chromatographies, filtration, ultrafiltration, salting out, solvent precipitation, solvent extraction, distillation, immunoprecipitation, SDS-polyacrylamide gel electrophoresis, isoelectric focusing, dialysis, and recrystallization.

By treating PlGF of the present invention with a suitable protein modification enzyme before or after purification, PlGF can be optionally modified and peptides can be removed partially. For example, trypsin, chymotrypsin, lysyl endopeptidase, protein kinase, glucosidase, and such are used as protein modification enzymes.

Subjects to be administered with pharmaceutical compositions (therapeutic agents) of the present invention are mammals. Mammals include, but are not limited to, humans, mice, rats, rabbits, guinea pigs, hamsters, dogs, cats, cows, horses, pigs, goats, and sheep.

The above-mentioned therapeutic agents can be administered orally or parenterally, but parenteral administration is preferred. Specific examples include injections, transnasal administrations, transpulmonary administrations, and transdermal administrations. For example, injections can be administered systemically or locally by intravenous injection, intramuscular injection, intraperitoneal injection, or subcutaneous injection.

When administering PlGF-encoding nucleic acids to a living body, viral vectors such as retrovirus, adenovirus, and Sendai virus, and non-viral vectors such as liposomes may be used. Examples of administration methods include in vivo methods and ex vivo methods.

A therapeutic agent of the present invention can be directly administered to patients alone, and alternatively it can be administered as a formulated pharmaceutical agent by known pharmaceutical methods. For example, it can be used in the form of an injection of a sterile solution or suspension with water or other pharmaceutically acceptable liquids. Furthermore, for example, it may be formulated by appropriately combining with pharmacologically acceptable carriers or vehicles, specifically sterilized water and physiological saline, emulsifiers, suspending agents, surfactants, stabilizers, vehicles, antiseptics, and such, and mixed in a unit dosage form required by generally accepted pharmaceutical procedures. The amount of active ingredient in these formulations is adjusted so that one can obtain an appropriate amount in the specified range.

Sterile compositions for injection can be formulated using vehicles such as distilled water for injection, according to standard protocols. Aqueous solutions used for injection include, for example, physiological saline and isotonic solutions containing glucose or other adjuvants such as D-sorbitol, D-mannose, D-mannitol, and sodium chloride. These can be used in conjunction with suitable solubilizers such as alcohol, specifically ethanol, polyalcohols such as propylene glycol and polyethylene glycol, and non-ionic surfactants such as Polysorbate 80™ and HCO-50.

Oils include sesame oils and soybean oils, and can be combined with solubilizers such as benzyl benzoate or benzyl alcohol. These may also be formulated with buffers, for example, phosphate buffers or sodium acetate buffers; analgesics, for example, procaine hydrochloride; stabilizers, for example, benzyl alcohol or phenol; or antioxidants. The prepared injections are typically aliquoted into appropriate ampules.

Furthermore, the administration dose can be appropriately selected according to the age and symptoms of the patient. The dose can be selected, for example, from the range of 0.0001 to 1,000 mg per kg of body weight. Alternatively, the dose may be, for example, in the range of 0.001 to 100,000 mg/patient. However, the pharmaceutical agents of the present invention are not limited to these doses.

Daily administration from the early stage of hypertension is preferred for the therapeutic agents of the present invention, particularly pravastatin. More specifically, in the case of humans, for example, daily administration from the 20th week of pregnancy or earlier is preferred. For example, in the case of mice, daily administration preferably from day 13, more preferably from day 10, and even more preferably from day 7 is preferred.

Furthermore, it is more preferable that daily administration of a therapeutic agent of the present invention is started before the onset of hypertension.

All prior art references cited herein are incorporated by reference into this description.

EXAMPLES

Herein below, the present invention will be specifically described further using the Examples, but the technical scope of the present invention is not to be construed as being limited thereto.

1. Method
Primers and PCR

Figure 2:
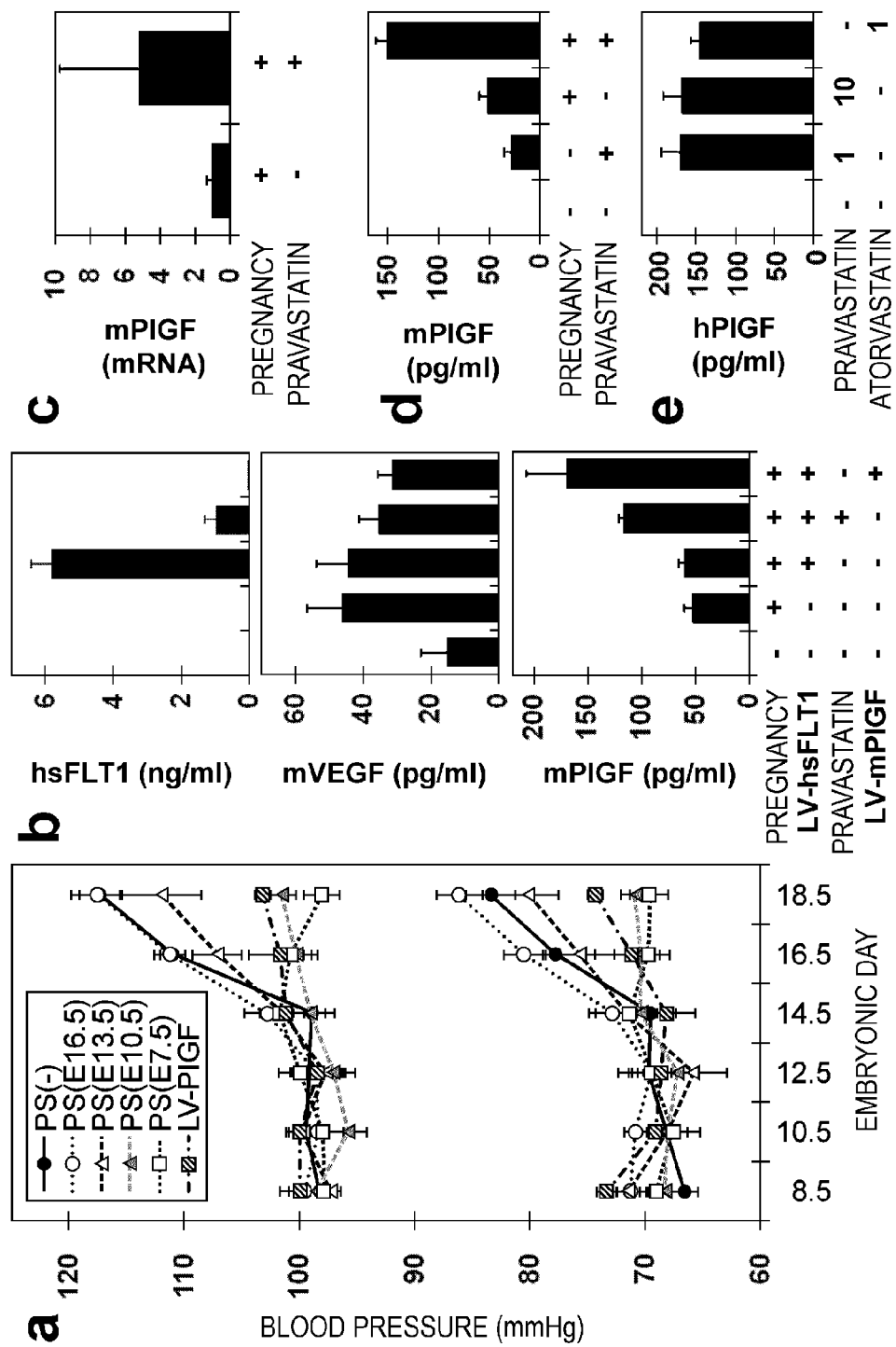
FIG. 2 shows in graphs that pravastatin (PS) improves pregnancy-induced hypertension syndrome by up-regulating PIGF. (a) Hypertension induced by the placenta-specific hsFLT1 expression was improved by pravastatin. Pravastatin (5 μg) was intraperitoneally administered to the female animals every day starting at the indicated days. (b) The concentrations of hsFLT1, mouse VEGF (mVEGF), and mouse PIGF (mPIGF) in the mother's blood were measured at E18.5. (c) mRNA extracted from the placenta at E18.5 was analyzed by quantitative RT-PCR. (d) Pravastatin (5 μg) was administered every day starting at E7.5 to non-pregnant and pregnant female mice that had not been treated with viral vector. The mPIGF concentration in the mother's blood was measured at E18.5. (e) HUVEC cells were cultured in a statin-containing medium, and 24 hours later, the concentrations of human VEGF (hVEGF) and human PIGF (hPIGF) in the supernatant were measured. 293T cells were used as a control.

The human sFLT1 (hsFLT1) cDNA was amplified by RT-PCR from HUVECs (Kurabo) with primers 5'-aaggatccgccgccatggtcagctactgggac-3' (SEQ ID NO: 7) and 5'-ttctcgagt-taatgttttacattactttgtgtg-3' (SEQ ID NO: 8). The mouse PlGF (mPlGF) cDNA was amplified by RT-PCR from E13.5 placenta with primers 5'-aagaattcgccaccatgctggtcatgaagctgttc-3' (SEQ ID NO: 9) and 5'-ttctcgagtcacgggtggggttcctcag-3' (SEQ ID NO: 10). In FIG. 1b, primers 5'-aagtgtgacgttgacatccg-3' (SEQ ID NO: 11) and 5'-gatccacatctgctggaagg-3' (SEQ ID NO: 12) were used for amplification of mActb, and primers 5'-ggctgagcataactaaatctgcc-3' (SEQ ID NO: 13) and 5'-ggaatgacgagctcccttccttca-3' (SEQ ID NO: 14) were used for amplification of hsFLT1. In FIG. 2c, primers 5'-catccgtaaagacctctatgccaac-3' (SEQ ID NO: 15) and 5'-atggagccaccgatccaca-3' (SEQ ID NO: 16) were used for amplification of mActb, and primers 5'-tgctgggaacaactcaacag-3' (SEQ ID NO: 17) and 5'-cctcatcagggtattcatcca-3' (SEQ ID NO: 18) were used for amplification of mPlGF.

Lentiviral Vectors

The HIV-I based, self-inactivating, lentiviral vector plasmid pLV-EGFP was described previously (Nat. Biotechnol. 2007 February; 25(2): 233-7). Other lentiviral vector plasmids pLV-hsFLT1 and pLV-mPGF were prepared by substituting an EGFP cDNA with an hsFLT1 cDNA or an mPlGF cDNA, respectively. Vesicular stomatitis virus glycoprotein-pseudotyped lentiviral vectors were generated, and the p24 gag antigen concentration was measured as described previously (Nat. Genet. 2000 June; 25(2): 217-22).

Mice and Lentiviral Transduction

Wild-type B6D2F1 female animals were superovulated by human chorionic gonadotropin (5 units) 48 hours after the intraperitoneal injection of pregnant mare's serum gonadotropin (5 units) and then mated with wild-type B6D2 F1 male animals. Two to four cell-stage embryos were collected from the female animals at 1.5 days after copulation, and then incubated in the kSOM medium (erbach BOR 1994) for two days to obtain blastocysts. Zona pellucida was removed in acidic Tyrode's solution (Sigma, Nicolson JCB 1975) to prepare zona pellucida-free blastocysts. Then, they were incubated individually for 4 hours in 5 μL of medium containing lentiviral vectors. The transduced blastocysts were washed three times and then transplanted into pseudo-pregnant ICR female animals. The present inventors transplanted ten blastocysts into each horn of the uterus. All animal experiments were approved by the Animal Care and Use Committee of the Research Institute for Microbial Diseases, Osaka University.

Statins

Pravastatin sodium salt (Cayman Chemical) was dissolved in 100% ethanol to produce a stock solution (1 mg/mL), which was diluted by sterile PBS (25 μg/mL) before use and intraperitoneally injected every day starting from E7.5 to E18.5 at 5 μg/animal unless specifically instructed otherwise.

Atorvastatin (Toronto Research Chemicals Inc.) was dissolved in 100% methanol to produce a stock solution (25 mg/mL), which was diluted by sterile PBS (12.5 μg/mL) before use.

For HUVEC cells, each of the stock solutions was added upon dilution to 1 μM or 10 μM in a culture medium.

Blood and Urinary Samples

Blood samples were allowed to clot and were centrifuged to prepare serum samples. Concentrations of hsFlT1, mVEGF, and mPlGF were measured with ELISA kits, according to the manufacturer's instructions (R&D system). Aspartate aminotransferase (AST) and alanine transaminase (ALT) were measured by Fuji dry-chem 3500V and dri-chem slides (Fuji Film co). Urine samples were collected at E18.5. Urine albumin and creatinine concentrations were measured by using the Fuji dry-chem 3500V and dri-chem slides (Fuji Film.co, Tokyo Japan).

Measurement of Blood Pressure

Blood pressure was measured by the tail-cuff method (Softron Ltd, Tokyo, Japan). The mice were lightly fixed in a small cage without anesthesia, and their blood pressure was measured after their behavior, heart rate, and blood pressure stabilized. After stabilization, both systolic and diastolic blood pressures were recorded at least five times until the stabilization became unstable. Mean values of both the systolic and diastolic blood pressures measured as mentioned above were used for further statistical analysis.

Histopathology of Placenta

Placentas collected from sacrificed mice were fixed in 4% paraformaldehyde (PFA)/PBS for 12 hours, and then subjected to further staining. Anti-CD31 antibody staining has been described previously. In brief, the PFA-fixed samples were rinsed with PBS for 4 hours, and soaked sequentially in 40%, 70%, and 100% methanol at 4° C. Sections prepared at a thickness of 5 µm were stained with an anti-mouse CD31 antibody (BD Biosciences) and visualized with an AlexaFluor 488-conjugated goat anti-rat IgG (Molecular Probes). Morphological alterations of the tissues were analyzed by Ehrlich hematoxylin-eosin staining Samples were visualized by using conventional microscopy (DM5500 B; Leica), and images were processed using the Adobe Photoshop CS3 software (Adobe Systems).

In Vitro Expression of PlGF as an Effect of Statin

HUVEC and HEK293T cells were plated at $2 \times 10^4$ and $1 \times 10^5$ cells per well in 6-well plates, respectively, and incubated under 5% $CO_2$ at 37° C. After 24 hours, the medium was replaced with a fresh medium containing or not containing a statin. The media collected after another 24 hours were centrifuged at 1,000×g, and the supernatants were subjected to ELISA.

Statistical Analyses

All values are expressed as mean±s.e.m. The present inventors used the two-tailed unpaired Student's t-test for comparison between groups, and P values<0.05 were considered as significant.

2. Results hsFLT1 was expressed specifically in the murine placenta throughout the gestational period to develop a novel animal model for pregnancy-induced hypertension syndrome (FIG. 1). The present inventors previously showed that when the trophectoderm cells of blastocysts are transduced with a lentiviral (LV) vector, placenta-specific gene integration and expression take place (Nat. Biotechnol. 2007 February; 25 (2): 233-7). According to this method, the present inventors transduced zona pellucida-free blastocysts with an hsFLT1-expressing LV vector (LV-hsFLT1), and transplanted these blastocysts into pseudo-pregnant female animals (FIG. 1a). Unless specifically indicated otherwise, blastocysts were transduced with the lentiviral vector at 100 ng-p24/mL throughout the experiment. As predicted by the present inventors, PCR and RT-PCR analyses demonstrated that integration and expression of the LV-hsFLT1 transgene was placenta-specific (FIG. 1b), but placenta-derived hsFLT1 was proven to circulate in the mother's blood (FIGS. 1c and d).

The hsFLT1 concentration in the mother's blood correlated with the amount of lentiviral vector at the time of blastocyst transduction (FIG. 1c). When LV-hsFLT1 was transduced at 100 ng-p24/mL, the circulating hsFLT1 concentration in the mother's body gradually increased during pregnancy, reaching an average value of 5.84±1.26 ng/mL at the embryonic age of 18.5 days (E18.5) (FIG. 1d), which was comparable to the sFLT1 concentration (4,382 pg/mL on average) in human patients (N Engl J. Med. 2004 Feb. 12; 350(7): 672-83. Circulating angiogenic factors and the risk of preeclampsia.). After the elevation of hsFLT1, the systolic as well as diastolic blood pressures significantly increased at E16.5 and continued during the rest of pregnancy (P<0.05, FIG. 1e). It should be noted that the blood pressure promptly reached a normal level postpartum, which mimics recovery after delivery of the placenta in human. The symptoms of hypertension were also observed in the group treated with LV-hsFLT1 at 20 ng-p24/mL, but not in the group treated at 4 ng-p24/mL (FIG. 1e). The pregnant female animals carrying the LV-hsFLT1-transduced placenta exhibited glomerulosclerosis (FIG. 4) and proteinuria (FIG. 10. These data indicated that the placenta-specific overexpression of hsFLT1 provides an animal model for pregnancy-induced hypertension syndrome.

Figure 4:
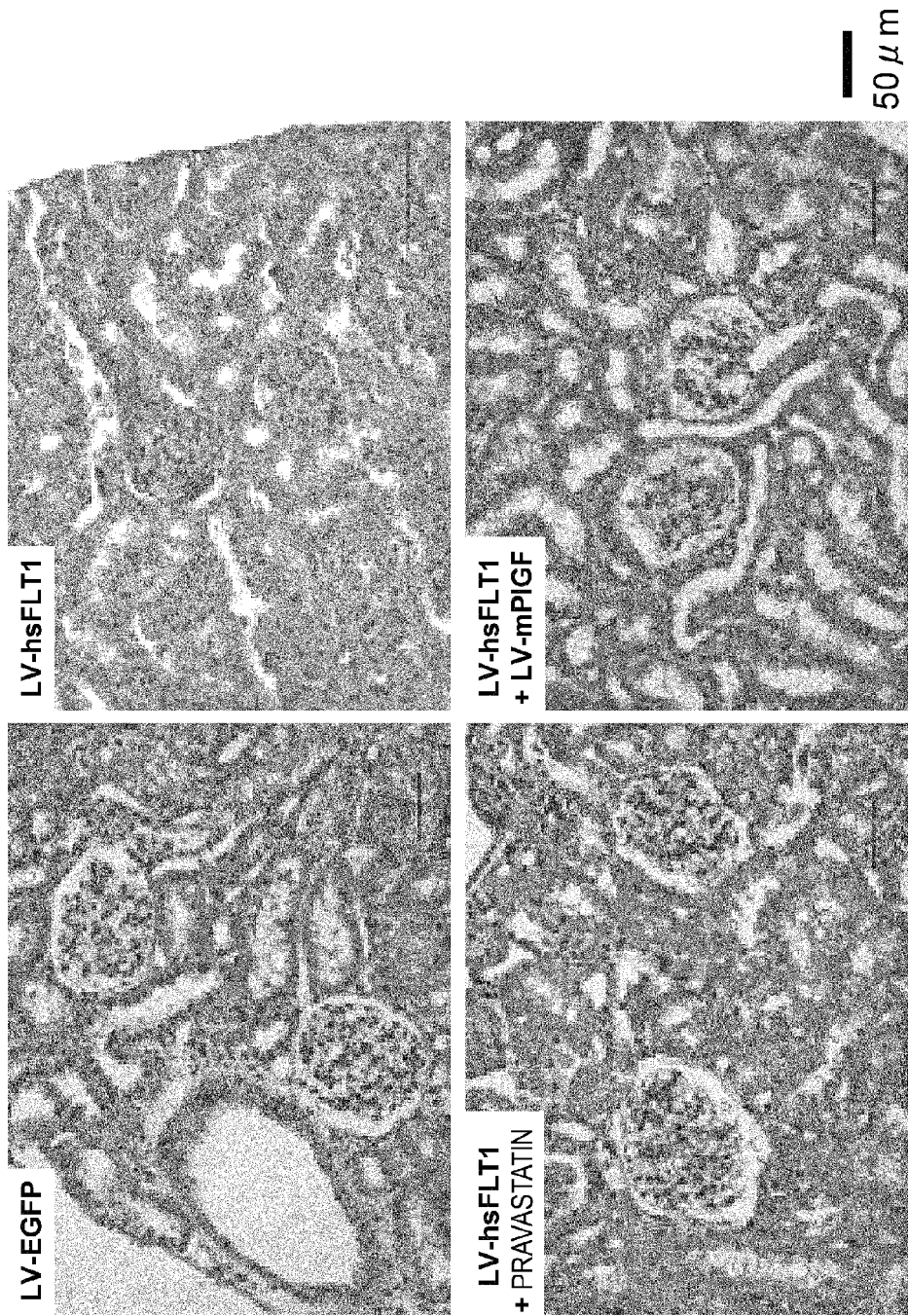
FIG. 4 shows in photographs the HE staining result of kidney sections collected from a female on the 18th day of pregnancy. The treatment is indicated in the upper left of each photograph. As compared to the control (upper left), shrinking of the kidney glomeruli was observed due to placenta-specific hsFLT1 overexpression (upper right). The pathology was recovered by administering pravastatin (lower left) or overexpressing mPIGF specifically in the placenta (lower right) from the seventh day of pregnancy.
Figure 5:
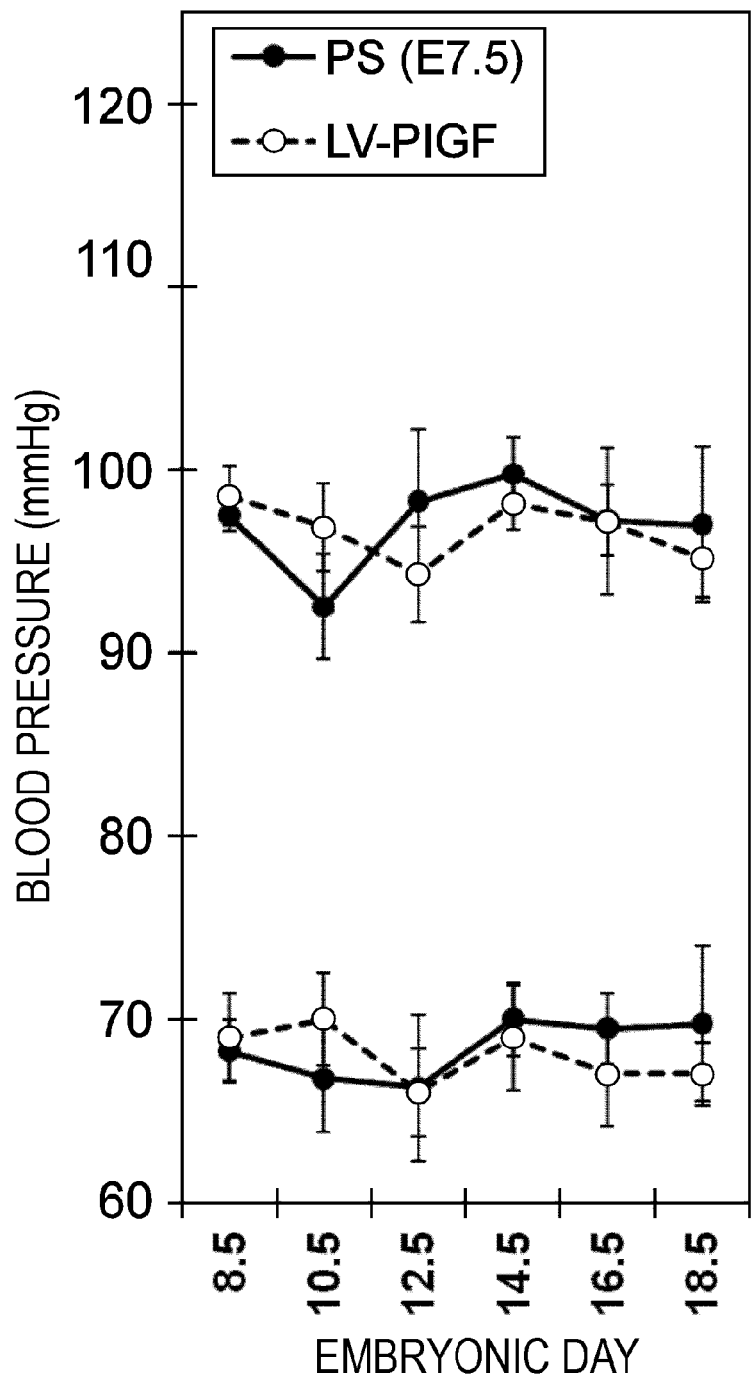
FIG. 5 shows in a graph changes in the blood pressure due to pravastatin (PS) administration or placenta-specific mPIGF overexpression. The blood pressure did not change even when pravastatin was administered to wild-type pregnant mice from the seventh day to the 18th day of pregnancy (solid line). Furthermore, even when mPIGF was overexpressed specifically in the placenta, the blood pressure did not change (dotted line).

Next, the present inventors used their model mice to examine the therapeutic effects of a HMG-CoA reductase inhibitor, pravastatin, on pregnancy-induced hypertension syndrome. Statins are generally used as drugs for hypercholesterolemia, but it has been recently reported that statins have a protective effect on vascular endothelial cells (Pharmacol Ther. 2009 April; 122(1): 30-43. Epub 2009 Jan. 23, Statins and cardioprotection—more than just lipid lowering?; and Circulation. 2002 Feb. 12; 105(6): 739-45. Statins have biphasic effects on angiogenesis). Moreover, pravastatin administration improved placental dysfunction and prevented miscarriages in a spontaneous-abortion model mouse (Blood. 2009 Apr. 23; 113(17): 4101-9. Epub 2009 Feb. 20, Pravastatin prevents miscarriages in mice: role of tissue factor in placental and fetal injury). To define its prophylactic/therapeutic effect, the present inventors intraperitoneally administered pravastatin at 5 µg/head, which is equivalent to a therapeutic dose of 10 mg/60 kg in human and the like. When pravastatin was administered every day from E10.5 or earlier, a prophylactic/therapeutic effect on hypertension was observed (FIG. 2a). Administration from E13.5 also similarly decreased the blood pressure, but the decrease was not significant. It should be noted that pravastatin is not hypotensive in normal pregnant female animals (FIG. 5). Glomerulosclerosis and proteinuria were similarly improved in the treated mice (FIG. 4 and Table 1). The P values in Table 1 are all t-test values in comparison to the control.

TABLE 1

| LV | n | ALBUMIN/CREATININE AVERAGE | P |
|---|---|---|---|
| LV-GFP | 12 | 5.27 ± 0.74 | — |
| LV-hsFLT1 | 14 | 7.47 ± 0.61 | 0.03 |
| LV-hsFLT1 + PRAVASTATIN | 8 | 4.06 ± 0.38 | 0.23 |
| LV-hsFLT1 + LV-mPlGF | 15 | 6.41 ± 0.61 | 0.24 |

Average ± S.E.M.

In the next experiment, the present inventors investigated how pravastatin improved sFLT1-induced hypertension. Since sFLT1 interacts with and antagonizes the angiogenic functions of VEGF and PlGF, the present inventors measured the placental mRNA levels and the maternal blood concentrations of these factors at E18.5 (FIGS. 2b and c). Pravastatin was administered every day from E7.5. Pravastatin did not affect the hsFLT1 mRNA level, but the circulating hsFLT1 was significantly decreased from 5.84±1.26 to 0.99±0.65 ng/mL (n=5, P<0.001) in the female animals carrying LV-hsFLT1-transduced placentas. The resulting hsFLT1 concentra tion was equal to or lower than the concentration in pregnant women with normal blood pressure (1,642 ng/mL on average; N Engl J. Med. 2004 Feb. 12; 350(7): 672-83. Circulating angiogenic factors and the risk of preeclampsia). mVEGF was not changed in terms of mRNA and protein levels (from 44.7±22.3 to 35.5±13.6 pg/mL, n=6, P=0.36). Interestingly, mPIGF was significantly induced by the pravastatin treatment (60.3±12.6 to 116.6±13.2 pg/ml; n=7; P<0.001). Accordingly, placental mPIGF mRNA increased approximately five-fold after the pravastatin treatment (FIG. 2c).

To determine whether pravastatin-induced PlGF counteracts sFLT1 in vivo, the present inventors simultaneously expressed mPIGF with hsFLT1 in the placenta by transducing the blastocyst with LV-hsFLT1 and LV-mPIGF (FIGS. 2a and b). As predicted, overexpression of mPIGF decreased hsFLT1 in the mother's blood (FIG. 2b), and improved hypertension (FIG. 2a). LV-mPIGF transduction alone did not show any hypotensive effects (FIG. 5). In addition to hypertension, glomerulosclerosis and proteinuria were similarly improved by mPIGF (Table 1 and FIG. 4). These data support the idea that pravastatin-induced PIGF counteracts sFLT1 and improves the symptoms of pregnancy-induced hypertension syndrome in vivo.

To determine whether pravastatin induces PIGF without influences from the LV vector or sFLT1, the present inventors administered pravastatin to wild-type female animals. The circulating mPIGF was significantly induced in the pregnant female animals from 52.4±20.2 pg/mL to 152.0±19.7 pg/mL (n=4, P<0.001, FIG. 3a). Surprisingly, mPIGF was also induced in the non-pregnant female animals from 0 pg/mL to 29.8±13.2 pg/mL (n=5, P<0.01, FIG. 3a). As far as the present inventors know, this is the first report that a therapeutic dose of pravastatin induces PIGF expression in vivo. Next, the present inventors examined whether pravastatin induces PIGF production in the vascular endothelial cells. Both pravastatin and atorvastatin induced PGF production in human umbilical vein endothelial cells (HUVECs). The statin treatment did not produce PIGF in the control human embryonic kidney (HEK293) cells (FIG. 3b). Statin has been reported to be effective for vascular dysfunction, but its mechanism is still unclear (Pharmacol Ther. 2009 April; 122(1): 30-43. Epub 2009 Jan. 23, Statins and cardioprotection—more than just lipid lowering?). The data obtained by the present inventors suggested that the ectopic expression of PIGF may explain the protective effect of statins on vascular endothelial cell dysfunction.

Figure 3:
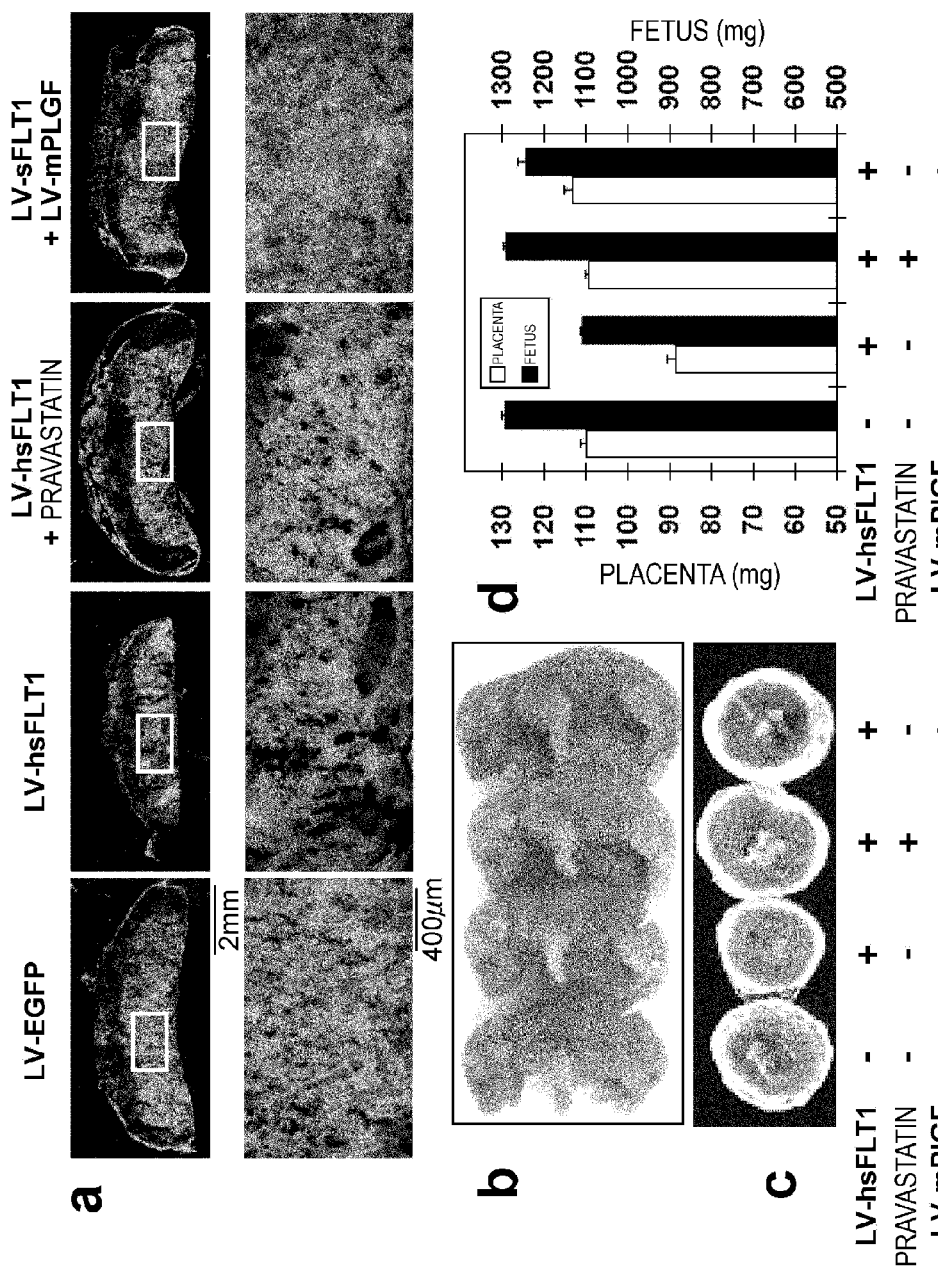
FIG. 3 shows in photographs and graphs that the pravastatin or LV-mPIGF treatment restored placental formation and ameliorated IUGR in pregnancy-induced hypertension syndrome. (a-d) Placenta-specific hsFLT1 overexpression impaired vasculogenesis in the placenta and caused IUGR. (a) Impaired vasculogenesis in the placenta was restored by pravastatin treatment or PIGF expression. Placentas were collected at E13.5, and PECAM1-expressing cells were stained with an anti-CD31 antibody. The white box in the upper panel is magnified in the lower panel. (b-d) Fetuses and placentas were collected by Caesarian section at E18.5. (b) Live pups. (c) Placentas. Photos were taken from the maternal side and fetal side (lower part). (d) Fetal weight and placental weight.

Finally, taking advantage of the present inventor's placenta-specific gene manipulation method, the present inventors evaluated the local effects of excess sFLT1 on placental formation and fetal development. When examined at E13.5, immunostaining of PECAM1 using an anti-CD31 antibody showed suppression of vascular bed development in the LV-hsFLT1-transduced placenta (FIG. 3a). When Caesarean section was performed at E18.5, both placenta and fetus from the LV-hsFLT1-treated female animals were smaller than those from the control LV-EGFP-treated group (FIGS. 3b to d), but the implantation rate and birth rate were equivalent (Table 2). The impaired placental formation and IUGR were ameliorated by the pravastatin treatment and the placenta-specific mPIGF expression (FIG. 3). These data support the idea that statin-induced PIGF counteracts sFLT1 and ameliorates impaired placental formation and IUGR in the pregnancy-induced hypertension syndrome models of the present inventors.

TABLE 2

IMPLANTATION RATE AND BIRTH RATE

| LV | n | GENE TRANSFER | IMPLANTATION RATE (%) | BIRTH RATE (%) |
|---|---|---|---|---|
| LV-GFP | 11 | 220 | 99 (45.0 ± 1.8) | 82 (37.3 ± 1.7) |
| LV-hsFLT1 | 11 | 220 | 100 (45.5 ± 2.0) | 85 (38.6 ± 2.5) |
| LV-hsFLT1 + PRAVASTATIN | 10 | 200 | 89 (44.5 ± 0.9) | 76 (38.0 ± 1.0) |
| LV-hsFLT1 + LV-mPIGF | 12 | 240 | 108 (45.0 ± 1.2) | 90 (37.5 ± 1.3) |

Average ± S.E.M.

The experiments conducted so far showed that VEGF improves hypertension (Hypertension. 2007 October; 50(4): 686-92. Epub 2007 Aug. 27, Recombinant vascular endothelial growth factor 121 attenuates hypertension and improves kidney damage in a rat model of preeclampsia). However, in the present inventors' system, the therapeutic effect of pravastatin depends on PIGF rather than on VEGF. This idea is also supported by the fact that recombinant PIGF improves hypertension induced by sFLT1 which was expressed by an adenovirus (Hypertension. 2009 November; 54(5): 1129-35. Epub 2009 Sep. 28, Effect of recombinant placental growth factor 2 on hypertension induced by full-length mouse soluble fms-like tyrosine kinase 1 adenoviral vector in pregnant mice). While the VEGFR1-mediated vasodilatory effect of PIGF cannot be excluded (Am J Physiol Heart Circ Physiol. 2008 March; 294(3): H1381-7. Epub 2008 Jan. 11, Placental growth factor is a potent vasodilator of rat and human resistance arteries), the present inventors' data suggested that the direct antagonizing effect of PIGF on sFLT1 is an important element during pravastatin treatment.

Regarding clinical applications of statins, teratogenicity is a major concern for pregnant women. The FDA classifies statins as category X and strongly discourages the prescription of statins during the first trimester. However, several recent examinations indicate that statins may be safe even in the first trimester (Reprod Toxicol. 2008 October; 26(2): 175-7. Epub 2008 Jul. 1, Prenatal exposure to HMG-CoA reductase inhibitors: effects on fetal and neonatal outcomes. Br J Clin Pharmacol. 2007 October; 64(4): 496-509. Epub 2007 May 15, Risk of congenital anomalies in pregnant users of statin drugs. Pregnancy outcomes after maternal exposure to simvastatin and lovastatin. Reprod Toxicol. 1996 November-December; 10(6): 439-46. Postmarketing surveillance of lovastatin and simvastatin exposure during pregnancy). The present inventors also did not notice any deformity in the pups of the pravastatin-treated female animals used in the experiments. While large-scale and accurate morphological examinations are necessary, statins are highly promising candidate substances for prevention/improvement of pregnancy-induced hypertension syndrome, in order to save numerous pregnant women and infants from morbidity and mortality worldwide.

Industrial Applicability

Model animals for pregnancy-induced hypertension syndrome that show placenta-specific expression of sFLT1, and methods for producing the model animals are provided by the present invention. Conventional model animals for pregnancy-induced hypertension syndrome have been produced by overexpressing a causative factor in the mother's body, and they are defective as disease models. On the other hand, in the model animals of the present invention, symptoms of hypertension appear along with placental growth as pregnancy continues, and symptoms of hypertension are improved by placental shedding at delivery.

Specifically, the model animals of the present invention have the following advantages compared to conventional model animals.
(1) Use of a lentiviral vector in a preferred embodiment leads to not transient but constitutive sFLT1 expression throughout the pregnancy period.
(2) While sFLT1 is conventionally expressed mainly in the liver by gene transfer into the mother's body, the method of the present invention expresses sFLT1 by introducing the gene transfer only into the placenta without gene transfer into the mother's body. This eliminates direct effects of viral vector infection on the mother's body, which has been conventionally impossible. Furthermore, it can exclude direct effects of sFLT1 gene expression in the mother's body.
(3) In the conventional method, since sFLT1 is expressed throughout the mother's body, the pathological condition is maintained regardless of delivery, whereas in the method of the present invention, the expression is placenta-specific; and thus the pathological condition is improved after delivery. Since humans follow the same course, one can say that this model better reflects the patient's pathological condition.

Furthermore, in the present invention, statins were found to improve the symptoms of pregnancy-induced hypertension syndrome, placental insufficiency, intrauterine growth retardation, glomerulosclerosis, and proteinuria. At the moment, the only existing methods for treating pregnancy-induced hypertension syndrome are delivery or removal of the placenta by Caesarian section. The economic effect is great with the added indication for statins as therapeutic agents for pregnancy-induced hypertension syndrome, affecting 5 to 7% of all pregnant women. Furthermore, the economic effect is also great because the burden on the obstetrical department caused by emergency Caesarian section, as well as the burden on neonatal ICU due to early Caesarian section and such can be lessened.

The invention claimed is:

1. A mouse pregnant with a mouse fetus, the placenta of said fetus comprises a lentiviral vector comprised of a human soluble fms-like tyrosine kinase 1 (sFLT1)-encoding nucleic acid sequence operatively inserted in said lentiviral vector in a manner such that the human sFLT1 protein is specifically expressed in said placenta, wherein said pregnant mouse exhibits symptom of a disease selected from the group consisting of pregnancy-induced hypertension syndrome, placental insufficiency, intrauterine growth retardation, glomerulosclerosis, and proteinuria; and
   wherein the human sFLT1 protein is expressed in said mouse placenta throughout a gestational period of said mouse fetus.

2. The pregnant mouse of claim 1, which is obtained by steps (a) to (c) below:
   (a) removing zona pellucida of a blastocyst of a mouse;
   (b) introducing a lentiviral vector comprising a human sFLT1-encoding nucleic acid sequence specifically into trophectoderm of the blastocyst obtained in step (a); and
   (c) transplanting the blastocyst obtained in step (b) into a superovulated female mouse.

3. The pregnant mouse of claim 2, wherein the superovulated female mouse is a Wild-Type B6D2F1 female mouse.

4. The pregnant mouse of claim 3, wherein the human sFLT1-encoding nucleic acid sequence comprises SEQ ID NO:1.

5. The pregnant mouse of claim 4, wherein the mouse exhibits symptoms of pregnancy-induced hypertension.

* * * * *